United States Patent
Sternby et al.

(10) Patent No.: US 10,137,233 B2
(45) Date of Patent: Nov. 27, 2018

(54) DETECTING PRESSURE PULSES IN A BLOOD PROCESSING APPARATUS

(71) Applicant: GAMBRO LUNDIA AB, Lund (SE)

(72) Inventors: Jan Sternby, Lund (SE); Mattias Holmer, Lund (SE); Bo Olde, Lund (SE); Kristian Solem, Kavlinge (SE); Anders Wallenborg, Trollsjovagen (SE); Per Hansson, Akarp (SE)

(73) Assignee: GAMBRO LUNDIA AB, Lund (SE)

( * ) Notice: Subject to any disclaimer, the term of this patent is extended or adjusted under 35 U.S.C. 154(b) by 383 days.

(21) Appl. No.: 14/651,730

(22) PCT Filed: Dec. 11, 2013

(86) PCT No.: PCT/EP2013/076233
§ 371 (c)(1),
(2) Date: Jun. 12, 2015

(87) PCT Pub. No.: WO2014/095524
PCT Pub. Date: Jun. 26, 2014

(65) Prior Publication Data
US 2015/0306293 A1 Oct. 29, 2015

Related U.S. Application Data

(60) Provisional application No. 61/738,569, filed on Dec. 18, 2012.

(30) Foreign Application Priority Data

Dec. 18, 2012 (SE) ..................................... 1251450

(51) Int. Cl.
*B01D 61/30* (2006.01)
*B01D 61/32* (2006.01)
(Continued)

(52) U.S. Cl.
CPC ............. *A61M 1/14* (2013.01); *A61B 5/7217* (2013.01); *A61M 1/1605* (2014.02);
(Continued)

(58) Field of Classification Search
CPC . A61B 5/021; A61B 5/02108; A61B 5/02116; A61B 5/02125; A61B 5/6866;
(Continued)

(56) References Cited

U.S. PATENT DOCUMENTS 4,960,128 A * 10/1990 Gordon .................. A61B 5/022
600/490
5,580,460 A    12/1996 Polaschegg
(Continued)

FOREIGN PATENT DOCUMENTS

EP       2319551       5/2011
JP    2010 18870       9/2010
(Continued)

OTHER PUBLICATIONS

International Search Report—PCT/EP2013/076233—dated Apr. 16, 2014—3 pages.
(Continued)

*Primary Examiner* — Joseph W Drodge
(74) *Attorney, Agent, or Firm* — K&L Gates LLP

(57) ABSTRACT

A monitoring device (7) operates on a pressure signal from a blood processing apparatus, e.g. a dialysis machine, which has an extracorporeal blood circuit connected to a vascular system of a subject for pumping blood through a dialyzer, and a treatment fluid supply system for pumping a treatment fluid through the dialyzer. The monitoring device (7) has a first input block (50) for obtaining a first pressure signal (y) from a first pressure sensor (6a) in the extracorporeal blood circuit, and a second input block (51) for obtaining a second pressure signal (w) from a second pressure sensor (6b) in the
(Continued)

treatment fluid supply system. An emulation block (56) generates, as a function of the second pressure signal (w), an emulated first pressure signal (y) which emulates a concurrent signal response of the first pressure sensor (6a), and a filtering block (53) generates a filtered signal (y) as a function of the first pressure signal (y) and the emulated first pressure signal (y), so as to suppress, in the filtered signal (}y) compared to the first pressure signal (y), signal interferences originating from the treatment fluid supply system (1b). A pulse detection block (54) processes the filtered signal (y_f) for detection of subject pulses originating from the subject.

21 Claims, 8 Drawing Sheets

(51) Int. Cl.
A61M 1/16 (2006.01)
A61M 1/36 (2006.01)
A61M 1/14 (2006.01)
A61B 5/00 (2006.01)

(52) U.S. Cl.
CPC ........ *A61M 1/1613* (2014.02); *A61M 1/3653* (2013.01); *A61M 1/3656* (2014.02); *B01D 61/30* (2013.01); *B01D 61/32* (2013.01); *A61M 1/3639* (2013.01); *A61M 2205/13* (2013.01); *A61M 2205/15* (2013.01); *A61M 2205/3303* (2013.01); *A61M 2205/3331* (2013.01); *A61M 2205/3344* (2013.01); *A61M 2205/50* (2013.01); *A61M 2230/04* (2013.01)

(58) Field of Classification Search
CPC ......... A61B 5/7217; A61B 5/024; A61B 5/72; A61B 5/7203; A61B 5/7271; A61M 1/36; A61M 1/3607; A61M 1/3621; A61M 1/3639; A61M 1/3653; A61M 1/3656; A61M 2205/3331; A61M 2230/04; A61M 2230/30; A61M 1/14; A61M 1/1613; A61M 1/1605; A61M 2205/3344; A61M 2205/3303; A61M 2205/50; A61M 2205/15; A61M 2205/13; A61M 1/16; A61M 1/1601; A61M 1/1603; A61M 2205/3653; G01L 19/00; B01D 61/30; B01D 61/22; B01D 61/32; B01D 2311/14
USPC .... 210/90, 97, 143, 645, 646, 740; 340/611; 600/485, 500, 501, 502; 604/5.01, 6.01, 604/6.09, 65, 67; 702/50, 66, 71, 72
See application file for complete search history.

(56) References Cited

U.S. PATENT DOCUMENTS

| | | | |
|---|---|---|---|
| 6,077,443 A | 6/2000 | Goldau | |
| 6,430,295 B1* | 8/2002 | Handel | G10K 11/345 381/71.11 |
| 6,471,646 B1* | 10/2002 | Thede | A61B 5/021 600/301 |
| 7,181,146 B1* | 2/2007 | Yorks | H04B 10/0799 398/195 |
| 7,317,409 B2* | 1/2008 | Conero | A61B 5/021 341/127 |
| 9,427,613 B2* | 8/2016 | Jordan | A63B 5/20 |
| 9,895,109 B2* | 2/2018 | Hansson | A61B 5/0215 |
| 2002/0113016 A1 | 8/2002 | Takai | |
| 2005/0065459 A1 | 3/2005 | Zhang et al. | |
| 2007/0024410 A1* | 2/2007 | Yazdi | G01K 1/024 338/13 |
| 2007/0112274 A1* | 5/2007 | Heitzmann | A61B 5/0002 600/485 |
| 2010/0028979 A1* | 2/2010 | Faulkner | A01N 1/0247 435/284.1 |
| 2010/0137777 A1 | 6/2010 | Kopperschmidt | |
| 2010/0192686 A1* | 8/2010 | Kamen | A61M 1/16 73/290 R |
| 2010/0234787 A1 | 9/2010 | Masaoka | |
| 2011/0040502 A1* | 2/2011 | Furmanski | A61M 1/3653 604/4.01 |
| 2011/0106466 A1* | 5/2011 | Furmanski | A61M 1/3653 702/51 |
| 2011/0112595 A1* | 5/2011 | Solem | A61M 1/3653 607/17 |
| 2011/0158331 A1* | 6/2011 | Kavaler | G08G 1/00 375/259 |
| 2013/0020237 A1* | 1/2013 | Wilt | A61M 1/1037 210/85 |
| 2013/0030357 A1* | 1/2013 | Yu | A61M 1/28 604/29 |
| 2016/0101227 A1* | 4/2016 | Norris | A61M 1/166 604/29 |

FOREIGN PATENT DOCUMENTS

| | | |
|---|---|---|
| WO | 2009156174 | 12/2009 |
| WO | 20009156175 | 12/2009 |
| WO | 2010149726 | 12/2010 |
| WO | 2011080190 | 7/2011 |
| WO | 2011080194 | 7/2011 |
| WO | 2012095066 | 7/2012 |

OTHER PUBLICATIONS

Written Opinion—PCT/EP2013/076233—dated Apr. 16, 2014—8 pages.
Prosecution history of U.S. Appl. No. 13/001,314 (now issued U.S. Pat. No. 9,442,036) filed Dec. 23, 2010.
Prosecution history of U.S. Appl. No. 13/380,631 (now issued U.S. Pat. No. 9,433,356) filed Mar. 16, 2012.
Prosecution history of U.S. Appl. No. 14/129,087 (now issued U.S. Pat. No. 9,427,513) filed Apr. 11, 2014.
Prosecution history of U.S. Appl. No. 12/988,146 (now issued U.S. Pat. No. 8,718,957) filed Oct. 15, 2010.
Prosecution history of U.S. Appl. No. 13/000,856 (now issued U.S. Pat. No. 8,715,216) filed Dec. 22, 2010.
Prosecution history of U.S. Appl. No. 14/270,246 (now issued U.S. Pat. No. 9,383,288) filed May 5, 2014.
Prosecution history of U.S. Appl. No. 13/519,532, filed Sep. 12, 2012.
Prosecution history of U.S. Appl. No. 14/123,397, filed Dec. 2, 2013.
Prosecution history of U.S. Appl. No. 13/519,483, filed Sep. 13, 2012.
Prosecution history of U.S. Appl. No. 13/519,559, filed Sep. 12, 2012.
Prosecution history of U.S. Appl. No. 14/234,527, filed May 5, 2014.
Prosecution history of U.S. Appl. No. 14/408,849, filed Dec. 17, 2014.
Prosecution history of U.S. Appl. No. 14/777,695, filed Sep. 16, 2015.
Prosecution history of U.S. Appl. No. 14/917,099, filed Mar. 7, 2016.
Prosecution history of U.S. Appl. No. 15/104,861, filed Jun. 15, 2016.

* cited by examiner

DETECTING PRESSURE PULSES IN A BLOOD PROCESSING APPARATUS

CROSS-REFERENCE TO RELATED APPLICATIONS

The present application is a National Phase of International Application No. PCT/EP 2013/076233, filed on Dec. 11, 2013, which claims priority to Sweden Patent Application No. 1251450-1, filed Dec. 18, 2012, and U.S. Provisional Application No. 61/738,569, filed Dec. 18, 2012, the entire contents of each of which is incorporated herein by reference and relied upon.

TECHNICAL FIELD

The present invention relates to a technique for enabling detection of pulses in a pressure signal from a blood processing apparatus, e.g. a dialysis machine, in particular pulses that originate from a patient which is connected to the blood processing apparatus.

BACKGROUND ART

In extracorporeal blood processing, blood is taken out of a human or animal subject, processed (e.g. treated) and then reintroduced into the subject by means of an extracorporeal blood flow circuit ("EC blood circuit") which is part of a blood processing apparatus. Generally, the blood is circulated through the EC blood circuit by a blood pump. In certain types of extracorporeal blood processing, the EC blood circuit includes an access device for blood withdrawal (e.g. a so-called arterial needle) and an access device for blood reintroduction (e.g. a so-called venous needle), which are inserted into a dedicated blood vessel access (e.g. fistula or graft) on the subject. Such extracorporeal blood processing includes hemodialysis, hemodiafiltration, hemofiltration, plasmapheresis, etc.

In extracorporeal blood processing, it is vital to minimize the risk for malfunctions in the EC circuit, since these may lead to a potentially life-threatening condition of the subject. Serious conditions may e.g. arise if the EC blood circuit is disrupted downstream of the blood pump, e.g. by a VND event (VND—Venous Needle Dislodgement), in which the venous needle comes loose from the blood vessel access. Such a disruption may cause the subject to be drained of blood within minutes.

VND may be detected during blood processing based on a pressure signal from a pressure sensor ("venous pressure sensor") on the downstream side of the blood pump in the EC circuit. Conventionally, VND monitoring is carried out by comparing one or more measured static pressure levels with one or more threshold values. However, it may be difficult to set appropriate threshold values, since the static pressure in the EC blood circuit may vary between treatments, and also during a treatment, e.g. as a result of the subject moving. Further, if the venous needle comes loose and gets stuck in bed sheets or the subject's clothes, the measured static pressure level might not change enough to indicate the potentially dangerous situation.

WO97/10013 proposes alternative techniques for VND monitoring based on the venous pressure signal. In one alternative, VND monitoring is based on detection of heart pulses in the pressure signal. The heart pulses represent pressure pulses produced by a patient's heart and transmitted from the patient's circulatory system to the venous pressure sensor via the blood vessel access and the venous needle. An absence of heart pulses in the pressure signal is taken as an indication of a possible VND event.

US2005/0010118, WO2009/156174 and US2010/0234786 disclose similar or alternative techniques of VND monitoring based on detection of heart pulses in the venous pressure signal.

WO2010/149726 discloses techniques for VND monitoring based on detection of physiological pulses other than heart pulses in the venous pressure signal. Such physiological pulses originate from the human subject, e.g. from reflexes, voluntary muscle contractions, non-voluntary muscle contractions, the breathing system, the autonomous system for blood pressure regulation or the autonomous system for body temperature regulation.

In order to provide a consistent and reliable VND monitoring based on heart pulses or other physiological pulses, it is important to ensure that the pressure signal is substantially free from pulsations that may interfere with the detection of the physiological pulses. For example, it is known that strong repetitive pulsations from the blood pump ("pump pulses") may be present in the pressure signal at a rate similar to the heart pulsations. In this respect, WO2009/156175 proposes techniques for filtering a pressure signal in the time domain for the purpose of eliminating (or suppressing) the pump pulses while retaining the physiological pulses. These techniques involve estimating the shape of the pump pulses, by obtaining a "predicted signal profile", at the relevant operating condition of the EC blood circuit and by subtracting the predicted signal profile from the pressure signal. In one implementation, a library of predicted signal profiles is recorded from a pressure sensor in the EC blood circuit in a reference measurement before treatment, e.g. during a priming phase or during a simulated treatment, at a plurality of different operating conditions of the EC blood circuit. In another implementation, the library of predicted signal profiles is generated by simulations using a mathematical model of the EC blood circuit. Based on the current operating condition of the EC blood circuit, a predicted signal profile may be selected from the library and used for eliminating the pump pulses. As an alternative to using pre-recorded or pre-calculated signal profiles, WO2009/156175 proposes recording the predicted signal profile during regular operation of the EC blood circuit, specifically by obtaining a pressure signal from a so-called "system pressure sensor" which is located between the blood pump and the dialyzer in the EC blood circuit. If the blood pump is a peristaltic pump, the system pressure sensor may be substantially isolated from the heart pulses, such that its pressure signal contains pump pulses and no heart pulses, or heart pulses that are significantly suppressed. Thus, in this special situation, the predicted signal profile of the pump pulses may be inferred from the pressure signal of the system pressure sensor and used for filtering the pressure signal generated by the venous pressure sensor.

The present Applicant has realized that the venous pressure sensor may also be responsive to pressure variations with an origin outside of the EC blood circuit, specifically from a supply system for dialysis fluid which is connected in fluid communication with the dialyzer. Such a supply system typically includes one or more valves and one or more fluid pumps that may generate pressure variations in the dialysis fluid, and these pressure variations are propagated via the blood processing unit into the EC blood circuit, where they may be detected by the venous pressure sensor. Depending on supply system, the pressure variations may take the form of a continuous, more or less randomly varying pressure level, or they may be manifested as distinct pulses that are generated at regular intervals or more irregularly, or a combination of both. Experiments indicate that the pressure variations from the supply system may seriously interfere with the detection of physiological pulses in the pressure signal from the venous pressure sensor.

The Applicant has found it difficult to apply the teachings of aforesaid WO2009/156175 to eliminate or suppress the pressure variations that originate from the supply system. For example, it is non-trivial to utilize a library of predicted signal profiles if the supply system is operated independently of the EC blood circuit and information about the operational state of the supply system is unavailable or incomplete. Furthermore, the use of predicted signal profiles is likely to result in insufficient removal of pressure variations that are non-repetitive or random, no matter if the predicted signal profiles are generated by reference measurements before the treatment, by reference measurements using a system pressure sensor in the EC blood circuit during the treatment, or by simulations. Furthermore, there are EC blood circuits that have no system pressure sensor.

Recently, it has also been shown to be possible to monitor and analyze the behavior of physiological pressure generators such as the heart or respiratory system, based on pressure recordings in the EC blood circuit. Various applications are found in WO2010/149726, WO2011/080189, WO2011/080190, WO2011/080191 and WO2011/080194.

Furthermore, WO2011/080188 proposes a technique for identifying and signaling a reverse placement of the devices for blood withdrawal and blood reintroduction in the vascular access by detecting and analyzing physiological pulses in a pressure signal recorded in the EC blood circuit.

All of these monitoring techniques presume that the physiological pulses can be reliably detected in the pressure signal.

SUMMARY

It is an objective of the invention to at least partly overcome one or more of the above-identified limitations of the prior art.

Another objective is to enable robust and reliable detection, in a pressure signal obtained in an extracorporeal blood circuit, of pulses that originate from a subject connected to the extracorporeal blood circuit.

Yet another objective is to provide a monitoring technique with reduced sensitivity to pressure variations in a monitored pressure signal, where the pressure variations originate from a supply system for treatment fluid in a blood processing apparatus.

A further objective is to provide an reliable technique for VND monitoring which is based on detection of physiological pulses in the pressure signal obtained from a venous pressure sensor.

One or more of these objectives, as well as further objectives that may appear from the description below, are at least partly achieved by a monitoring device, an apparatus for blood processing, a monitoring method, and a computer-readable medium according to the independent claims, embodiments thereof being defined by the dependent claims.

A first aspect of the invention is a monitoring device, comprising: a first input block configured to obtain a first pressure signal from a first pressure sensor, which is arranged in an extracorporeal blood circuit to detect pressure variations in blood which is pumped through a blood processing unit in the extracorporeal blood circuit by a blood pumping device, wherein the extracorporeal blood circuit is connected to a vascular system of a subject; a second input block configured to obtain a second pressure signal from a second pressure sensor, which is arranged in a treatment fluid supply system to detect pressure variations in a treatment fluid which is pumped through the blood processing unit by the treatment fluid supply system; an emulation block configured to generate, as a function of the second pressure signal, an emulated first pressure signal which emulates a concurrent signal response of the first pressure sensor; a filtering block configured to generate a filtered signal as a function of the first pressure signal and the emulated first pressure signal, so as to suppress, in the filtered signal compared to the first pressure signal, signal interferences originating from the treatment fluid supply system; and a pulse detection block configured to process the filtered signal for detection of subject pulses originating from the subject.

The inventive technique operates to suppress, in the first pressure signal, disturbances that originate from the treatment fluid supply system and correspond to pressure waves that enter the extracorporeal blood circuit via the blood processing device. Since the pressure waves originate from the treatment fluid supply system, they will also generate signal components in the second pressure signal from the second pressure sensor in the treatment supply system. In the inventive technique, an emulated first pressure signal is generated, as a function of the second pressure signal, to emulate a concurrent signal response of the first pressure sensor. In other words, the appearance of the disturbances in the first pressure signal are estimated based on the signal components in the second pressure signal. When the first pressure signal is filtered using the emulated first pressure signal, the disturbances will be suppressed in the resulting filtered signal. This will improve the ability to detect the subject pulses, if present, in the first pressure signal. It should be noted that the inventive technique enables suppression of both periodic and non-period disturbances in the first pressure signal since it dynamically emulates the signal response of the first pressure sensor based on the signal response of the second pressure sensor.

In one embodiment, the emulated first pressure signal is generated as a time sequence of emulated signal values, and wherein the emulation block is configured to generate each emulated signal value to represent an instant signal response of the first pressure sensor as a function of one or more preceding signal values in the second pressure signal. The emulation block may be configured to generate each emulated signal value to represent an instant signal response of the first pressure sensor as a function of preceding signal values in the second pressure signal and as a function of preceding signal values in the first pressure signal. Alternatively or additionally, the filtering block may be configured to subtract each emulated signal value from a corresponding signal value of the first pressure signal to generate a filtered signal value in the filtered signal.

In one embodiment, the emulation block is configured to, in the emulated first pressure signal, emulate the signal response of the first pressure sensor with respect to magnitude, shape and timing of the signal interferences originating from the treatment fluid supply system.

In one embodiment, the emulation block is configured to generate the emulated first pressure signal using a first model function which includes a set of model parameters, wherein the set of model parameters define a weighted sum of preceding signal values within a moving time window of fixed length in the second pressure signal and, optionally, preceding signal values within a further moving time window of fixed length in the first pressure signal. The first model function may be a Controlled AutoRegressive model or a Controlled AutoRegressive Moving Average model.

In one embodiment, the emulation block is configured to update the set of model parameters as a function of time, preferably recursively.

In one practical implementation, the monitoring device is configured to repeatedly perform a processing sequence that comprises: obtaining, by the first input block, a signal value of the first pressure signal; obtaining, by the second input block, a signal value of the second pressure signal; retrieving, by the emulation block, an emulated signal value of the emulated first pressure signal, the emulated signal value being calculated in a preceding processing sequence; generating, by the filtering block, a filtered signal value by subtracting the emulated signal value from the signal value of first pressure signal; updating, by the emulation block, a measurement vector $\varphi(s)$ to include the signal value of the second pressure signal, such that the measurement vector contains the preceding signal values within the moving time window for a subsequent processing sequence; optionally updating, by the emulation block, the measurement vector $\varphi(s)$ to include the signal value of the first pressure signal, such that the measurement vector contains the preceding signal values within the further moving time window for the subsequent processing sequence; and calculating, by the emulation block and as a function of the set of model parameters and the updated measurement vector, an emulated signal value for use in a forthcoming processing sequence. The emulation block may be further configured to recursively compute, in each processing sequence, at least during a start-up phase of the monitoring device, a vector $x_e(s)$ containing values of the set of model parameters according to:

$$\begin{cases} x_e(s) = x_e(s-1) + [P(s-1)\cdot\varphi(s)/(\lambda+\varphi(s)^T\cdot P(s-1)\cdot\varphi(s))]\cdot[y(s)-\varphi(s)^T\cdot x_e(s-1)] \\ P(s) = [P(s-1) - P(s-1)\cdot\varphi(s)\cdot\varphi(s)^T\cdot P(s-1)/(1+\varphi(s)^T\cdot P(s-1)\cdot\varphi(s))]/\lambda + R \end{cases}$$

wherein $x_e(s-1)$ is the vector containing values of the set of model parameters as computed in the preceding processing sequence, $y(s)$ is the signal value of the first pressure signal obtained in the current processing sequence, $\varphi(s)$ is the measurement vector before said updating, $P(s)$ is a matrix, $\lambda$, is a global weighting factor that is smaller than or equal to 1, and R is a constant positive semidefinite matrix. In one implementation, the emulation block is configured to evaluate $[y(s)-\varphi(s)^T\cdot x_e(s-1)]$ by obtaining the filtered signal value generated by the filtering block in the current processing sequence.

In one embodiment, the global weighting factor is smaller than 1, $\lambda<1$.

In one embodiment, at least a subset of the constant values in R are non-zero.

In one embodiment, the emulation block is configured to generate the emulated first pressure signal by use of a FIR (Finite Impulse Response) filter or an IIR (Infinite Impulse Response) filter.

In one embodiment, the first and second input blocks are configured to perform a preparatory filtering to essentially eliminate pressure pulsations that originate from the blood pump in the first pressure signal and the second pressure signal, respectively.

In one embodiment, the extracorporeal blood circuit and the treatment fluid supply system are included in an apparatus for extracorporeal blood processing, and wherein the first and second input blocks are configured to perform a preparatory filtering to essentially eliminate, in the first second pressure signal and the second pressure signal, respectively, periodic pressure pulsations that originate in the apparatus for extracorporeal blood processing.

In one embodiment, the second pressure sensor is arranged to sense the subject pulses, and the monitoring device further comprises a third input block for obtaining a third pressure signal from a third pressure sensor, which is arranged in the extracorporeal blood circuit so as to sense the subject pulses and be essentially isolated from pressure variations originating from the treatment fluid supply system, and the emulation block comprises a first sub-block configured to generate, as a function of the third pressure signal, an emulated second pressure signal which emulates a concurrent signal response of the second pressure sensor, a second sub-block configured to generate a filtered second pressure signal by subtracting the emulated second pressure signal from the second pressure signal, and a third sub-block configured to generate the emulated first pressure signal as a function of the filtered second pressure signal. The first sub-block may be configured to, in the emulated second pressure signal, emulate the signal response of the second pressure sensor with respect to the subject pulses. In one embodiment, the extracorporeal blood circuit extends from a blood withdrawal device, which is connected to the vascular system of the subject, to a blood return device, which is connected to the vascular system of the subject, wherein the first pressure sensor is arranged downstream of the blood pumping device and the blood processing unit in the extracorporeal blood circuit, said monitoring device being configured to signal a dislodgement of the blood return device based on a detected absence of subject pulses in the filtered signal by the pulse detection block.

In one embodiment, the extracorporeal blood circuit extends from a blood withdrawal device, which is connected to the vascular system of the subject, to a blood return device, which is connected to the vascular system of the subject, wherein the first pressure sensor is arranged downstream of the blood pumping device and the blood processing unit in the extracorporeal blood circuit, and the third pressure sensor is arranged upstream of the blood pumping device and the blood processing unit in the extracorporeal blood circuit, said monitoring device being configured to signal a dislodgement of the blood return device based on a detected absence of subject pulses in the filtered signal by the pulse detection block.

A second aspect of the invention is an apparatus for extracorporeal blood processing, said apparatus comprising an extracorporeal blood circuit for connection to the vascular system of a subject; a blood processing unit in the extracorporeal blood circuit; a blood pumping device in the extracorporeal blood circuit operable to pump blood through the blood processing unit; a treatment fluid supply system operable to pump treatment fluid through the blood processing unit; a first pressure sensor arranged in the extracorporeal blood circuit to detect pressure variations in the blood which is pumped through the blood processing unit; a second pressure sensor arranged in the treatment fluid supply system to detect pressure variations in the treatment fluid which is pumped through the blood processing unit, said apparatus further comprising the monitoring device of the first aspect.

A third aspect of the invention is a monitoring method, comprising: obtaining a first pressure signal from a first pressure sensor, which is arranged in an extracorporeal blood circuit to detect pressure variations in blood which is pumped through a blood processing unit in the extracorporeal blood circuit, wherein the extracorporeal blood circuit is connected to the vascular system of a subject; obtaining a second pressure signal from a second pressure sensor, which is arranged in a treatment fluid supply system to detect pressure variations in a treatment fluid which is pumped through the blood processing unit by the treatment fluid supply system; generating, as a function of the second pressure signal, an emulated first pressure signal which emulates a concurrent signal response of the first pressure sensor; generating a filtered signal as a function of the first pressure signal and the emulated first pressure signal, so as to suppress, in the filtered signal compared to the first pressure signal, signal interferences originating from the treatment fluid supply system; and processing the filtered signal for detection of subject pulses originating from the subject.

In one embodiment, the emulated first pressure signal is generated as a time sequence of emulated signal values, and each emulated signal value is generated to represent an instant signal response of the first pressure sensor as a function of one or more preceding signal values in the second pressure signal. In this embodiment, each emulated signal value may be generated to represent an instant signal response of the first pressure sensor as a function of preceding signal values in the second pressure signal and as a function of preceding signal values in the first pressure signal. Alternatively or additionally, the step of generating the filtered signal may comprise subtracting each emulated signal value from a corresponding signal value of the first pressure signal to generate a filtered signal value in the filtered signal.

In one embodiment, the step of generating the emulated first pressure signal comprises: emulating, in the emulated first pressure signal, the signal response of the first pressure sensor with respect to magnitude, shape and timing of the signal interferences originating from the treatment fluid supply system.

In one embodiment, the step of generating the emulated first pressure signal comprises: generating the emulated first pressure signal using a first model function which includes a set of model parameters, such that the set of model parameters define a weighted sum of preceding signal values within a moving time window of fixed length in the second pressure signal and, optionally, preceding signal values within a further moving time window of fixed length in the first pressure signal. The first model function may be a Controlled AutoRegressive model or a Controlled AutoRegressive Moving Average model. In one embodiment, the method further comprises updating the set of model parameters as a function of time, e.g. recursively.

In one practical implementation, the method repeatedly performs a processing sequence that comprises: obtaining, in the step of obtaining the first pressure signal, a current signal value of the first pressure signal; obtaining, in the step of obtaining the second pressure signal, a current signal value of the second pressure signal; retrieving, in the step of generating the emulated first pressure signal, a current emulated signal value of the emulated first pressure signal, the current emulated signal value being calculated in a preceding processing sequence; generating, in the step of generating the filtered signal, a current filtered signal value by subtracting the current emulated signal value from the current signal value of first pressure signal; updating a measurement vector $\varphi(s)$ to include the current signal value of the second pressure signal, such that the measurement vector contains the preceding signal values within the moving time window for a subsequent processing sequence; optionally updating the measurement vector $\varphi(s)$ to include the current signal value of the first pressure signal, such that the measurement vector contains the preceding signal values within the further moving time window for the subsequent processing sequence; and calculating, in the step of generating the emulated first pressure signal and as a function of the set of model parameters and the updated measurement vector, a emulated signal value for use in a forthcoming processing sequence. The method may further comprise: recursively computing, in each processing sequence, at least during a start-up phase of the method, a vector $x_e(s)$ containing values of the set of model parameters according to:

$$\begin{cases} x_e(s) = x_e(s-1) + [P(s-1) \cdot \varphi(s)/(\lambda + \varphi(s)^T \cdot P(s-1) \cdot \varphi(s))] \cdot [y(s) - \varphi(s)^T \cdot x_e(s-1)] \\ P(s) = [P(s-1) - P(s-1) \cdot \varphi(s) \cdot \varphi(s)^T \cdot P(s-1)/(1 + \varphi(s)^T \cdot P(s-1) \cdot \varphi(s))]/\lambda + R \end{cases}$$

wherein $x_e(s-1)$ is the vector containing values of the set of model parameters as computed in the preceding processing sequence, $y(s)$ is the current signal value of the first pressure signal, $\varphi(s)$ is the measurement vector before said updating, $P(s)$ is a matrix, $\lambda$, is a global weighting factor that is smaller than or equal to 1, and R is a constant positive semidefinite matrix. In one implementation, $[y(s)-\varphi(s)^T \cdot x_e(s-1)]$ may be replaced by the current filtered signal value.

In one embodiment, the global weighting factor is smaller than 1, $\lambda<1$.

In one embodiment, at least a subset of the constant values in R are non-zero.

In one embodiment, the emulated first pressure signal is generated by use of a FIR (Finite Impulse Response) filter or an IIR (Infinite Impulse Response) filter.

In one embodiment, the steps of obtaining the first and second pressure signals comprises a respective filtering step to essentially eliminate pressure pulsations that originate from the blood pump in the first pressure signal and the second pressure signal, respectively.

In one embodiment, the extracorporeal blood circuit and the treatment fluid supply system are included in an apparatus for extracorporeal blood processing, and the steps of obtaining the first and second pressure signals comprises a respective step of filtering to essentially eliminate, in the first second pressure signal and the second pressure signal, respectively, periodic pressure pulsations that originate in the apparatus for extracorporeal blood processing.

In one embodiment, the second pressure sensor is arranged to sense the subject pulses, and the method further comprises a step for obtaining a third pressure signal from a third pressure sensor, which is arranged in the extracorporeal blood circuit so as to sense the subject pulses and be essentially isolated from pressure variations originating from the treatment fluid supply system, and the step of generating the emulated first pressure signal comprises: a step of generating, as a function of the third pressure signal, an emulated second pressure signal which emulates a concurrent signal response of the second pressure sensor, a step of generating a filtered second pressure signal by subtracting the emulated second pressure signal from the second pressure signal, and a step of generating the emulated first pressure signal as a function of the filtered second pressure signal. The step of generating the emulated second pressure signal may comprise: emulating, in the emulated second pressure signal, the signal response of the second pressure sensor with respect to the subject pulses. In one embodiment, the extracorporeal blood circuit extends from a blood withdrawal device, which is connected to the vascular system of the subject, to a blood return device, which is connected to the vascular system of the subject, and the first pressure sensor is arranged downstream of the blood pumping device and the blood processing unit in the extracorporeal blood circuit, and the third pressure sensor is arranged upstream of the blood pumping device and the blood processing unit in the extracorporeal blood circuit, wherein the method comprises a step of signaling a dislodgement of the blood return device based on a detected absence of subject pulses in the filtered signal.

In one embodiment, the extracorporeal blood circuit extends from a blood withdrawal device, which is connected to the vascular system of the subject, to a blood return device, which is connected to the vascular system of the subject, and the first pressure sensor is arranged downstream of the blood pumping device and the blood processing unit in the extracorporeal blood circuit, wherein the method comprises a step of signaling a dislodgement of the blood return device based on a detected absence of subject pulses in the filtered signal.

A fourth aspect of the invention is a computer-readable medium comprising computer instructions which, when executed by a processor, cause the processor to perform the method of the third aspect.

A fifth aspect of the invention is a monitoring device, comprising: means for obtaining a first pressure signal from a first pressure sensor, which is arranged in an extracorporeal blood circuit to detect pressure variations in blood which is pumped through a blood processing unit in the extracorporeal blood circuit by a blood pumping device, wherein the extracorporeal blood circuit is connected to a vascular system of a subject; means for obtaining a second pressure signal from a second pressure sensor, which is arranged in a treatment fluid supply system to detect pressure variations in a treatment fluid which is pumped through the blood processing unit by the treatment fluid supply system; means for generating, as a function of the second pressure signal, an emulated first pressure signal which emulates a concurrent signal response of the first pressure sensor; means for generating a filtered signal as a function of the first pressure signal and the emulated first pressure signal, so as to suppress, in the filtered signal compared to the first pressure signal, signal interferences originating from the treatment fluid supply system; and means for processing the filtered signal for detection of subject pulses originating from the subject.

Any one of the above-identified embodiments of the third aspect may be adapted and implemented as an embodiment of the fifth aspect.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

DETAILED DESCRIPTION OF EXAMPLE EMBODIMENTS

Figure 1:
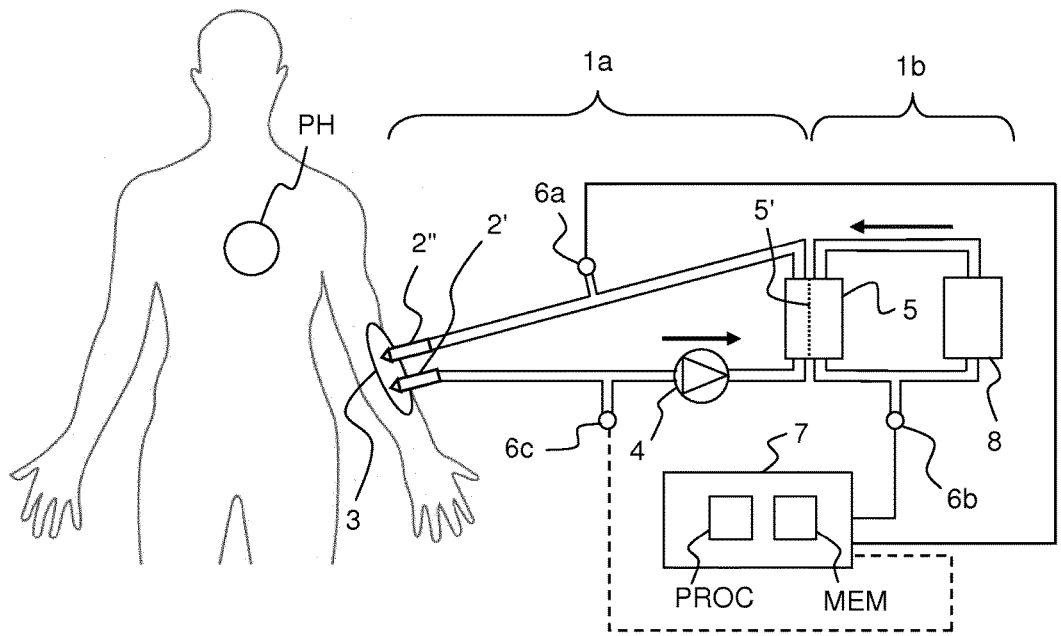
FIG. 1 a schematic diagram of an extracorporeal blood processing apparatus attached to a human subject.

Throughout the description, the same reference numerals are used to identify corresponding elements.

FIG. 1 illustrates a human subject which is connected to an extracorporeal blood flow circuit 1a by way of access devices 2', 2" inserted into a dedicated vascular access 3 (also known as "blood vessel access") on the subject. The extracorporeal blood flow circuit 1a (denoted "EC circuit" in the following) is configured to communicate blood to and from the cardiovascular system of the subject. In one example, the EC circuit 1a is part of an apparatus for blood processing, such as a dialysis machine (cf. 1 in FIG. 10). In the illustrated example, a blood pump 4 draws blood from the vascular access 3 via access device 2' and pumps the blood through a blood processing unit 5 and back to the vascular access 3 via access device 2". Thus, when both access devices 2', 2" are connected to the vascular access 3, the EC circuit 1a defines a blood path that starts and ends at the vascular access 3. The EC circuit 1a may be seen to comprise a "venous side" which is the part of the blood path located downstream of the blood pump 4, and an "arterial side" which is the part of the blood path located upstream of the blood pump 4.

The blood processing unit 5 may be any type of blood filtering device, such as a coil dialyzer, a parallel plate dialyzer, a hollow fiber dialyzer, etc. For simplicity, the blood processing unit 5 is denoted "dialyzer" in the following. The dialyzer 5 has a blood side and a treatment fluid side separated by a semipermeable membrane 5'. The blood side is connected as part of the EC circuit 1a, and the treatment fluid side is connected as part of a supply system for treatment fluid 1b (denoted "TF circuit" in the following).

The TF circuit 1b is arranged to pump a treatment fluid through the treatment fluid side of the dialyzer 5, whereby solutes are transported over the membrane 5' due to a concentration gradient and/or ultrafiltrate is transported over the membrane 5' due to a pressure gradient. The skilled person understands that the TF circuit 1b may include a plurality of functional components such as a source of fresh treatment fluid, a receptacle/drain for spent treatment fluid, one or more pumps, balancing chambers, valves, heaters, conductivity sensors, etc. For simplicity, these components are collectively represented by a generic box 8 in FIG. 1.

The EC circuit 1a includes a pressure sensor 6a on the venous side of the EC circuit 1 (denoted "venous pressure sensor" or "venous sensor"), and a pressure sensor 6c on the arterial side of the EC circuit 1 (denoted "arterial pressure sensor" or "arterial sensor"). The venous and arterial sensors 6a, 6c provide a respective time-varying signal that represents the pressure in the blood on the venous side ("venous signal") and the arterial side ("arterial signal"), respectively. In the following, the venous signal is denoted $y_{raw}$ and the arterial signal is denoted $v_{raw}$.

Figure 10:
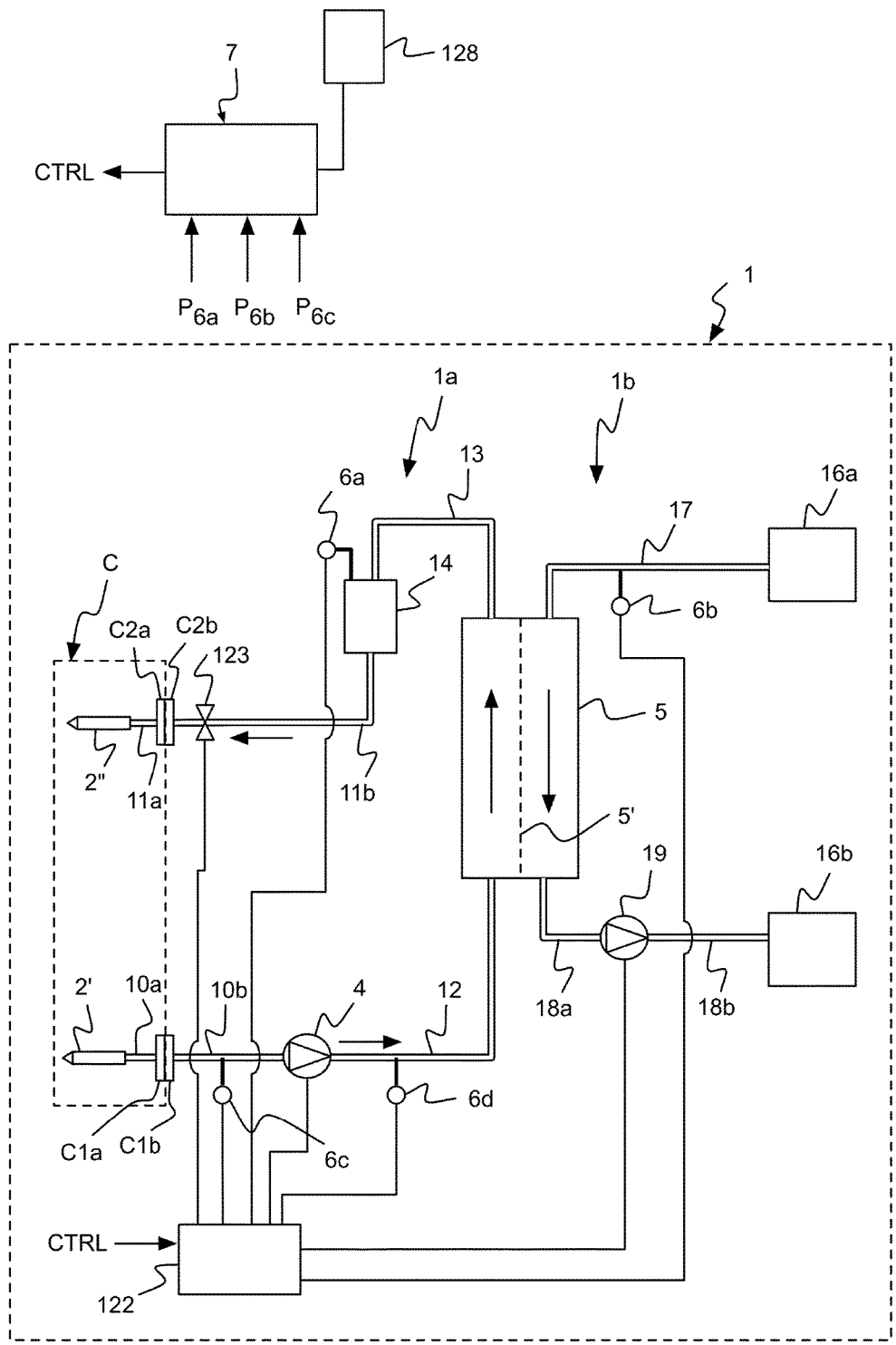
FIG. 10 is a schematic view of a dialysis machine and an inventive monitoring device.

Furthermore, a pressure sensor 6b (denoted "TF pressure sensor" or "TF sensor") is arranged in the TF circuit 1b to provide a time-varying signal that represents the pressure in the treatment fluid ("TF signal"). The TF signal is denoted $u_{raw}$ in the following. The TF sensor 6b may have any placement in the TF circuit 1b, e.g. downstream of the dialyzer 5, as shown in FIG. 1, or upstream of the dialyzer 5, as shown in FIG. 10.

A monitoring device 7 is connected to the sensors 6a, 6b, 6c by way of a respective data line to acquire and process the time-varying electric signals $y_{raw}$, $v_{raw}$, $u_{raw}$. The dashed data line from the arterial sensor 6a to the monitoring device 7 indicates that the use of the arterial signal $v_{raw}$ is optional, as will be described further below.

Specifically, the monitoring device 7 comprises processing circuitry adapted to filter the venous signal $y_{raw}$, for the purpose of enabling or facilitating detection of "subject pulses" in the venous signal. A "pulse" is a set of data samples that defines a local increase or decrease (depending on implementation) in signal magnitude within a time-dependent signal. The "subject pulses" represent pressure waves that are generated by one or more physiological sources PH in the subject and propagate through the cardiovascular system of the subject to the vascular access 3, and via the access device 2" to the venous sensor 6a, which produces corresponding subject pulses in the venous signal. The subject pulses may form, in the venous signal, a train of pulses from the respective physiological source PH, where each subject pulse represents a pressure wave generated by the respective physiological source PH. To the extent that subject pulses from different physiological sources PH are present in the venous signal, these subject pulses may, but need not, be superimposed in the venous signal. The pressure waves also enter the arterial side of the EC circuit 1a via the access device 2' and reach the arterial sensor 6c, which also produces corresponding subject pulses. The magnitude, shape and timing of the subject pulses may differ between the venous and arterial signals. Depending on the configuration of the EC circuit 1a, the dialyzer 5 and the TF circuit 1b, the pressure waves may also reach the TF sensor 6b, which then produces corresponding subject pulses in the TF signal. As used herein, a "pressure wave" is a mechanical wave in the form of a disturbance that travels or propagates through a material or substance. In the context of the following examples, the pressure waves propagate in the cardiovascular system of the subject, the blood path of the EC circuit 1a and the TF circuit 1b at a velocity that typically lies in the range of about 3-20 ms.

The physiological source PH may be any pulsatile physiological phenomenon such as the heart, the breathing system, the autonomous system for blood pressure regulation, the autonomous system for body temperature regulation, reflex actions, voluntary muscle contractions and non-voluntary muscle contractions. It is also conceivable the physiological source PH is a mechanical device which is attached to the subject and which shakes, vibrates or presses on the skin of the patient so as to generate the pressure waves. In another alternative, such a mechanical device may be attached to a support for the subject, e.g. a bed. In the following examples, however, it is assumed that the subject pulses originate from the subject's heart and are denoted "heart pulses". However, the inventive technique is applicable irrespective of the origin of the subject pulses.

The monitoring device may be configured to detect the subject pulses in the venous signal for the purpose of identifying a so-called venous needle dislodgment (VND), i.e. a dislodgement of venous access device 2" from the vascular access 3. Alternatively or additionally, if the source pulses originate from a physiological phenomenon in the subject, the monitoring device 7 may be configured to process the subject pulses for detecting, presenting, tracking and predicting vital signs of the subject. Further examples are given below in relation to FIG. 10.

Generally, the venous sensor 6a does not only measure subject pulses, but also various disturbances caused by pressure variations in the blood at the venous sensor 6a.

The disturbances may include both periodic and non-periodic components, and they may originate from both the EC circuit 1a and the TF circuit 1b. The blood pump 4 is known to generate strong, periodic disturbances ("pump pulses") in all of the signals $y_{raw}$, $v_{raw}$, $u_{raw}$. Other disturbances may originate from valves, clamps, and further blood pump(s) in the EC circuit 1a. The disturbances originating from the EC circuit 1a may be eliminated or at least significantly suppressed in all of the signals $y_{raw}$, $v_{raw}$, $u_{raw}$ by applying known filtering techniques, e.g. as indicated in the Background section. Alternatively, these disturbances may be eliminated by temporary disabling the EC circuit 1a, and the blood pump 4 in particular.

The present Applicant has found that, for the purpose of ensuring a consistent detection of the subject pulses, it is often not sufficient to suppress the pump pulses and other disturbances from the EC circuit 1a in the venous signal $y_{raw}$, since the venous signal $y_{raw}$ is also affected by pressure variations coming from the TF circuit 1b. These pressure variations propagate from the treatment fluid via the membrane 5' into the blood and show up as disturbances in the venous signal $y_{raw}$. The disturbances from the TF circuit 1b may be of the same magnitude as the subject pulses in the venous signal $y_{raw}$, or even much stronger, and may significantly interfere with the detection of the subject pulses. The disturbances from the TF circuit 1b may be period or non-periodic, or both, depending on the configuration of the TF circuit 1b. Periodic disturbances may, e.g., be caused by the regular operation of pumps, valves, etc in the TF circuit 1b, and non-periodic disturbances may, e.g., be caused by changes in the main flow rate of treatment fluid through the TF circuit 1b, and by irregular switching of valves in the TF circuit 1b. For example, the main flow rate may be actively changed by a control system for the TF circuit 1b, or it may be changed more or less randomly by occurrence of air bubbles in the treatment fluid. In certain implementations, the non-periodic disturbances may form an essentially continuous, time-varying signal component in the venous signal $y_{raw}$. It is also conceivable that the disturbances that enter the EC circuit 1a via the TF circuit 1b have an actual origin outside the TF circuit 1b. From the perspective of the venous sensor 6a, as located in the EC circuit 1a, these disturbances also come from the TF circuit 1b.

The disturbances from the TF circuit 1b are generally much smaller in the arterial signal $v_{raw}$, or even non-existent, at least if the blood pump 4 is of an occluding type, e.g. a peristaltic pump. Such a pump may act as a barrier to pressure variations and effectively dampen the pressure variations from the TF circuit 1b. These pressure variations may still reach the arterial sensor 6c by propagating along the venous side of the EC circuit 1a, into the vascular access 3 via the access device 2", and into the arterial side of the EC circuit 1a via the access device 2'. However, the pressure variations will be significantly dampened on this propagation path and, from a practical perspective, the disturbances from the TF circuit 1b are in most cases negligible in the arterial signal $v_{raw}$.

Embodiments of the invention relate to methods and structures in the monitoring device 7 for eliminating disturbances from the TF circuit 1b in the venous signal, or at least significantly suppressing these disturbances in relation to the subject pulses in the venous signal. Depending on implementation, the monitoring device 7 may use digital components or analog components, or a combination thereof, for receiving and processing signals. For example, the device 7 may be a computer, or a similar data processing device, with adequate hardware for acquiring and processing signals in accordance with different embodiments of the invention. Embodiments of the invention may be implemented by software instructions that are supplied on a computer-readable medium for execution by a processor PROC in conjunction with an electronic memory MEM in the device 7, as indicated in FIG. 1.

Figure 2:
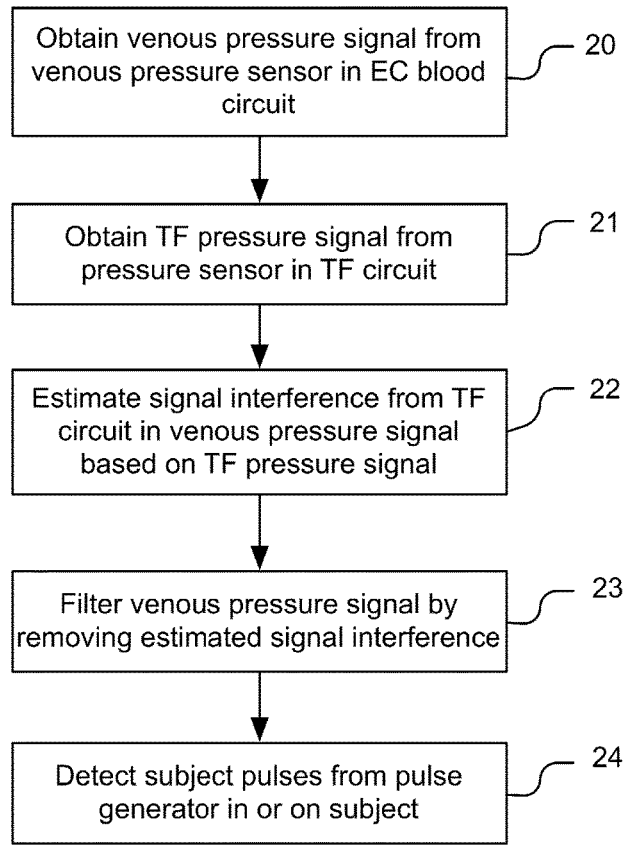
FIG. 2 illustrates principal steps of an inventive monitoring method as applied to the apparatus in FIG. 1.

FIG. 2 illustrates principal steps carried out by the device 7 in one embodiment, given in the context of FIG. 1. Thus, the device 7 obtains the venous signal $y_{raw}$ from the venous sensor 6a (step 20), and the TF signal $u_{raw}$ from the TF sensor 6b (step 21). Then, in step 22, the appearance of the disturbances (signal interferences) from the TF circuit 1b in the venous signal $y_{raw}$ is estimated based on the TF signal $u_{raw}$ using a suitable model function. The result of step 22 is thus an "emulated venous signal", which represents how the signal interferences are likely to be represented in the venous signal $y_{raw}$. The emulated venous signal is designated by $\hat{y}$ in the following. The model function is thus suitably designed to predict the magnitude, shape and timing of the signal interferences in the venous signal $y_{raw}$ given the magnitude, shape and timing of the signal interferences in the TF signal $u_{raw}$. In step 23, the estimated signal interference is removed from the venous signal $y_{raw}$, e.g. by subtracting the emulated venous signal $\hat{y}$ from the venous signal $y_{raw}$, to render a filtered signal $y_f$. Then, the filtered signal $y_f$ is processed for detection of the subject pulses (step 24). Step 24 may be implemented using known techniques, e.g. those presented in the Background section.

Since the TF sensor 6b is likely to receive all pressure waves that propagate from the TF circuit 1b into the EC circuit 1a, the signal interferences in the TF signal $u_{raw}$ may be seen to represent all disturbances from the TF circuit 1b that may emerge in the venous signal $y_{raw}$. It is thus realized that, provided that the model function is designed to adequately generate the emulated venous signal $\hat{y}$, the filtering step 23 is capable of suppressing both periodic and non-periodic disturbances from the TF circuit 1b in the venous signal $y_{raw}$.

In one embodiment, the model function is a physical model of the hydraulic system between the TF sensor 6b and the venous sensor 6a, and is based on a representation of how pressure waves are transmitted from one or more sources to the sensors 6a, 6b and give rise to the signal interferences at the respective sensor. Such a model function is typically tailored to the design of the circuits 1a, 1b and the location and type of the source(s) that cause the signal interferences.

In another embodiment, the model function is based on an input/output model and is designed to directly estimate the emulated venous signal $\hat{y}$; based on the TF signal $u_{raw}$, and optionally also based on the venous signal $y_{raw}$. Such a model function may be more generally applicable. Examples of input/output models are given below in relation to FIGS. 8-9.

Depending on model function, it may be necessary to pre-process the venous signal $y_{raw}$ and/or the TF signal $u_{raw}$ before steps 22 and 23 for removal or suppression of the above-mentioned pump pulses and other periodic disturbances that originate from the EC circuit 1a. For example, the use of an input/output model may require (or at least benefit from) that the disturbances from the EC circuit 1a are smaller in magnitude than the disturbances from the TF circuit 1b in the signals that are input to the model function. Of course, pre-processing may be omitted if the blood pump 4 is disabled during acquisition of the signals $y_{raw}$, $u_{raw}$ in steps 20 and 21. Additionally or alternatively, the pre-processing may involve other operations, such as re-sampling, removal of offset, high frequency noise and supply voltage disturbances, etc. As used herein, the pre-processed venous signal is denoted by y, and the pre-processed TF signal is denoted by u.

In a variant, the pre-processing is implemented to remove or suppress further periodic disturbances in the signals $y_{raw}$, $u_{raw}$, i.e. not only pump pulses and other periodic disturbances from the EC circuit 1a, but also periodic disturbances from the TF circuit 1b. Such filtering of periodic disturbances may be accomplished using the techniques disclosed in aforesaid WO2009/156175, or the techniques disclosed in Applicant's co-pending U.S. provisional application US61/671,192, which was filed on Jul. 13, 2012 and is incorporated herein by reference. By removing/suppressing all periodic disturbances by pre-processing, the filtering step 23 will primarily remove/suppress non-periodic disturbances from the TF circuit 1b.

Figure 3A:
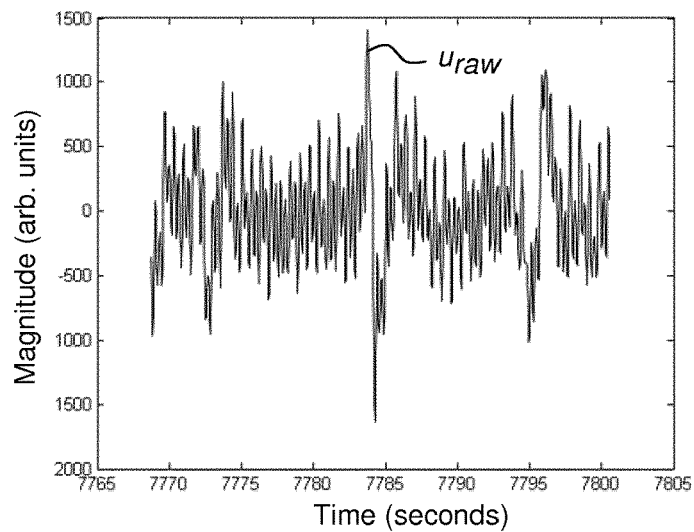
FIGS. 3A-3F are examples of time-varying signals retrieved from pressure sensors in the apparatus in FIG. 1 and generated by processing according to FIG. 2.
Figure 3B:
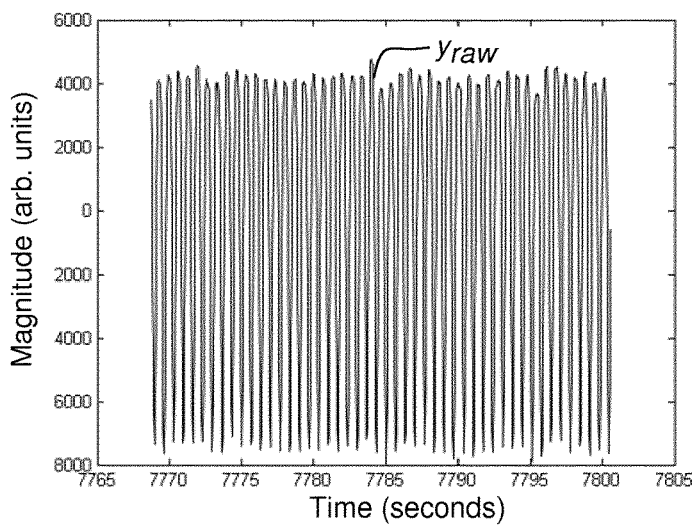
Figure 3C:
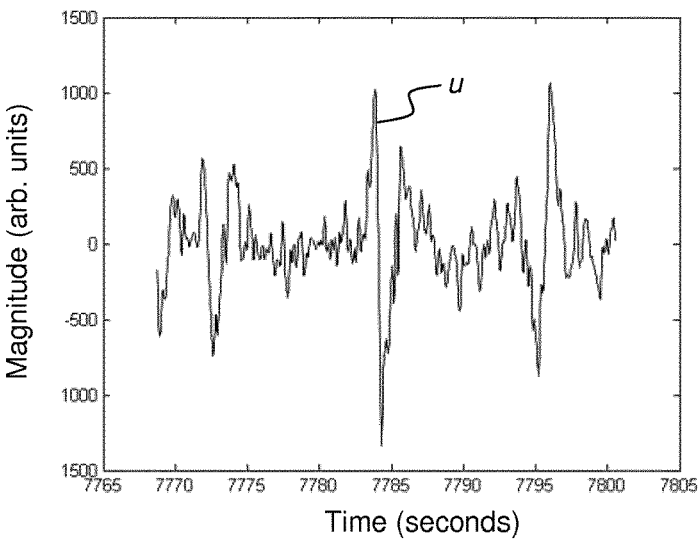
Figure 3D:
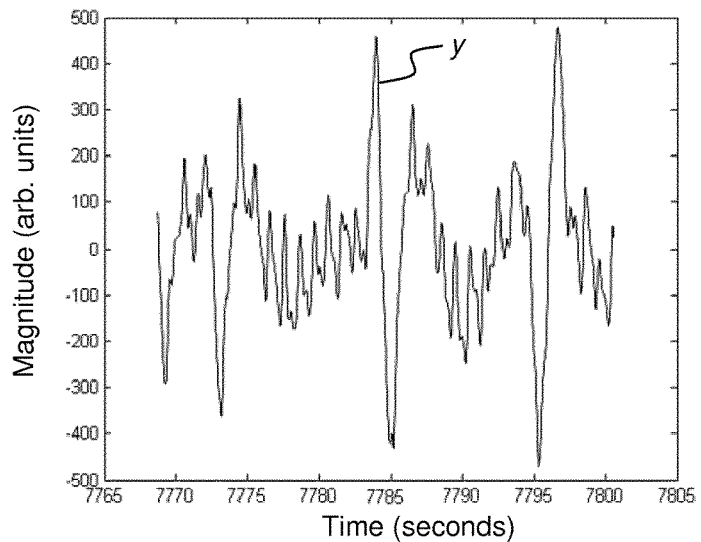
Figure 3E:
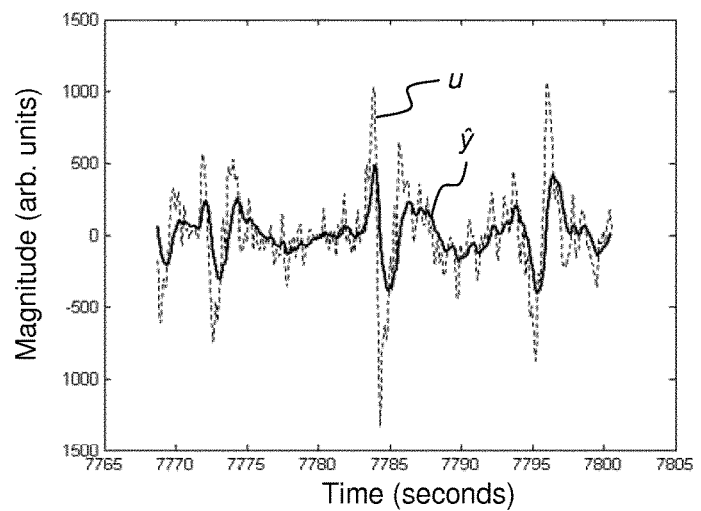
Figure 3F:
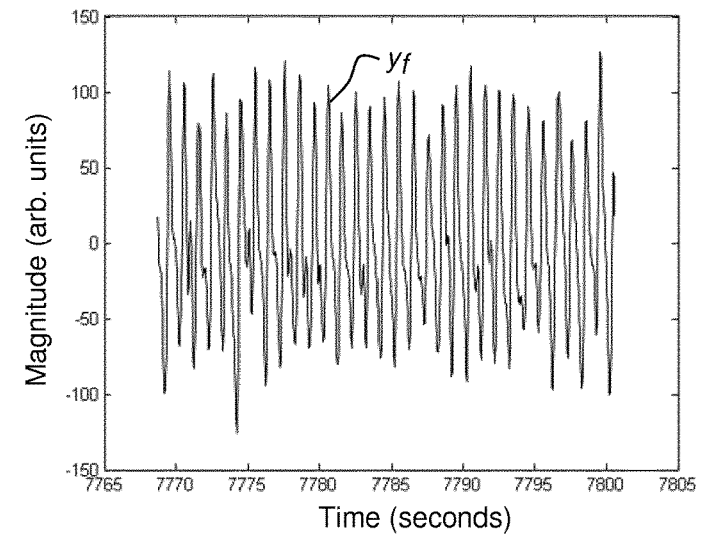

The operation of the device 7 in accordance with FIG. 2 is further exemplified in FIGS. 3A-3D, which are examples of time-dependent signals that may be acquired and generated by steps 20-23 in FIG. 2. FIG. 3A is an example of a TF signal $u_{raw}$ acquired by the device 7 from the TF sensor 6b in FIG. 1, and FIG. 3B is an example of a venous signal $y_{raw}$ acquired by the device 7 from the venous sensor 6a in FIG. 1. The TF signal $u_{raw}$ includes signal interferences from the TF circuit 1b and signal interferences (pump pulses) from the EC circuit 1a. The venous signal $y_{raw}$ includes strong signal interferences (pump pulses) from the EC circuit 1a, subject pulses (heart pulses) from the subject, and signal interferences from the TF circuit 1b. FIGS. 3C and 3D illustrate the TF signal u and venous signal y, respectively, which are obtained after pre-processing of $u_{raw}$ and $y_{raw}$ for removal of pump pulses. Thus, the TF signal u includes (mainly) signal interferences from the TF circuit 1b, and the venous signal y includes (mainly) subject pulses (heart pulses) from the subject and signal interferences from the TF circuit $1b$. It may be noted that, in this example, the pump pulses are about 10 times stronger than the signal interferences from the TF circuit $1b$ in the venous signal $y_{raw}$, and of the same magnitude as the signal interferences from the TF circuit $1b$ in the TF signal $u_{raw}$. FIG. 3E illustrates an emulated venous signal ŷ; which is obtained by applying the Controlled AutoRegressive model function described below in relation to FIGS. 8-9. For comparison, the emulated venous signal ŷ; is given in relation to the TF signal u (dashed line). As expected, the emulated venous signal ŷ; is a time-shifted and attenuated version of the TF signal u. FIG. 3F illustrates the resulting filtered signal $y_f$ which is obtained by subtracting the emulated venous signal ŷ; in FIG. 3E from the venous signal y in FIG. 3D. The filtered signal $y_f$ includes heart pulses, and essentially all signal interferences from the TF circuit $1b$ have been eliminated. As seen, the heart pulses appear with a rate of ca 60 Hz.

Figure 4:
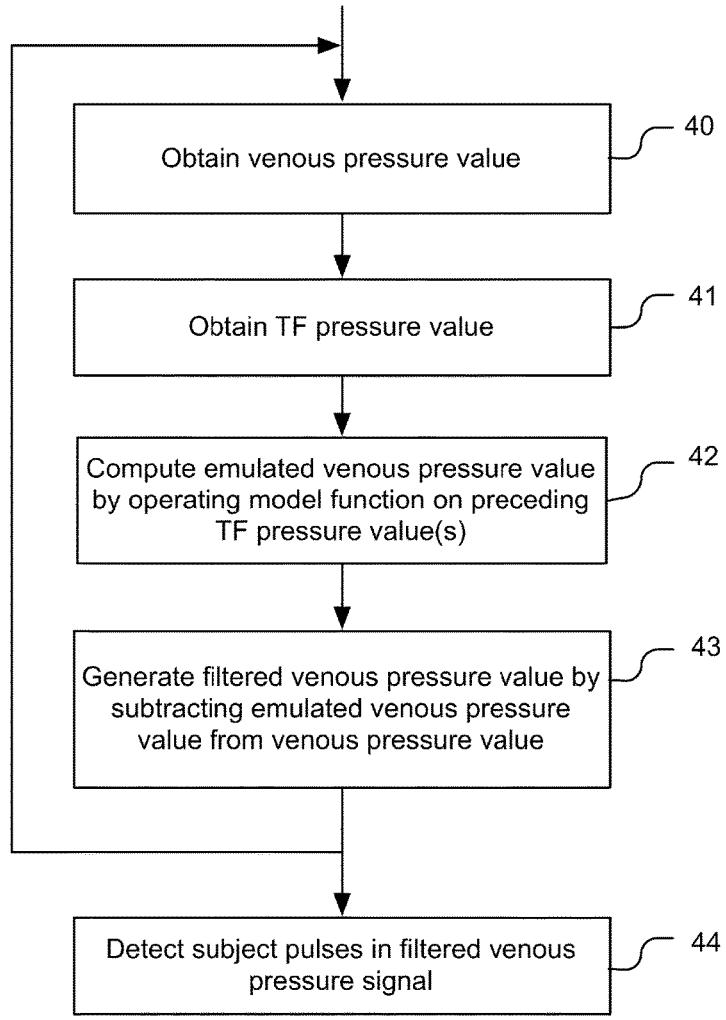
FIG. 4 is a flow chart of a monitoring method according to an embodiment.

FIG. 4 is a flowchart of a monitoring method that may be executed by the device 7 to generate the filtered signal $y_f$. The method in FIG. 4 is an implementation of the principal steps in FIG. 2 and repeatedly executes a sequence of steps 40-43 to generate the filtered signal $y_f$. Each loop of steps 40-43 forms a filtering operation that results in a filtered signal value at a current time point. The method in FIG. 4 thus enables real-time generation of the filtered signal $y_f$. The illustrated method also involves a step 44 of detecting subject pulses in the filtered signal $y_f$. Step 44 is shown as being separate from the filtering operation, since step 44 may operate independently of the steps 40-43 to detect the subject pulses among the filtered signal values. For example, step 44 may operate on buffered filtered signal values to identify the subject pulses in overlapping or non-overlapping time windows in the filtered signal. However, it is also conceivable that step 44 is executed each time a filtered signal value is generated by the filtering operation.

For each current time point t, the filtering operation involves a step 40 of obtaining a venous pressure value $y_{raw}(t)$ from the venous sensor $6a$, and a step 41 of obtaining a TF pressure value $u_{raw}(t)$ from the TF sensor $6b$. The following discussion assumes that steps 40, 41 also involve the above-mentioned pre-preprocessing, resulting in signal values y(t) and u(t). However, as noted above, such pre-processing may be omitted. In step 42, an emulated venous signal value ŷ(t) is computed, and in step 43 a filtered signal value $y_f(t)$ is generated by subtracting the emulated signal venous value ŷ(t) from the venous signal value y(t). The implementation of step 42 is dependent on model function, but generally the emulated signal value ŷ(t) is computed based on at least one preceding TF signal value, i.e. a signal value generated by step 41 at a preceding time point, e.g. the immediately preceding time point t−1. The input/output model described below in relation to FIGS. 8-9 uses a plurality of TF signal values and a plurality of venous signal values generated at preceding time points.

Figure 5:
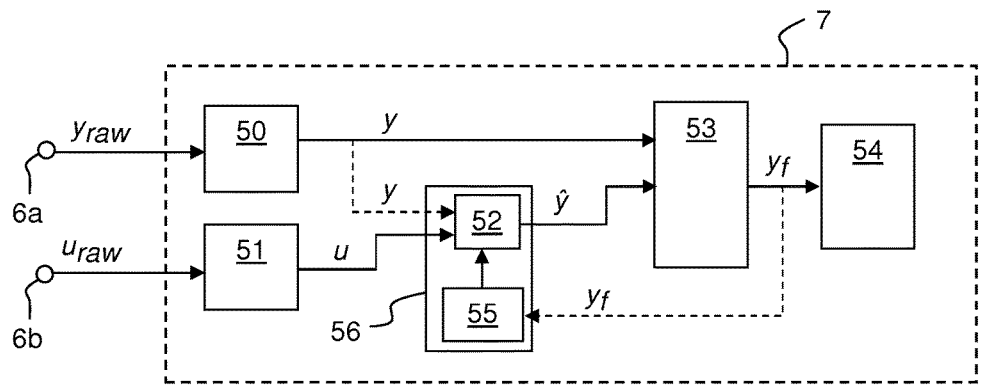
FIG. 5 is a block diagram of a structure for implementing the method in FIG. 4.

FIG. 5 is a block diagram of a structure for implementing the method of FIG. 4 in the device 7. In the illustrated embodiment, the device 7 includes input blocks 50, 51, an emulation block 56, a subtraction block 53, and a detection block 54. Although not shown, a control block may be provided to synchronize the operation of the blocks 50-56, and the blocks 50-56 may exchange data via an electronic memory (cf. MEM in FIG. 1).

The input block 50 implements step 40 in FIG. 4 and is arranged to obtain the venous signal $y_{raw}$ from the venous sensor $6a$ and output a sequence of venous signal values y(t). The input block 51 implements step 41 and is arranged to obtain the TF signal $u_{raw}$ from the TF sensor $6b$ and output a sequence of TF signal values u(t). The blocks 56, 53 are configured to receive or retrieve individual signal values y(t), u(t) generated by the input blocks 50, 51. Block 56 includes an emulation sub-block 52 which implements step 42 and is configured to compute a sequence of emulated signal values ŷ(t), based on the sequence of TF signal values u(t), and optionally based on the sequence of venous signal values y(t). Block 53 implements step 43 and is configured to compute a sequence of filtered signal values $y_f(t)$, based on the sequence of venous signal values y(t) and the sequence of emulated signal values ŷ(t). Block 54 implements step 44 and is configured to detect subject pulses in the sequence of filtered signal values $y_f(t)$. In the illustrated example, block 56 also includes a sub-block 55 which is configured to intermittently or continuously update the model function used by sub-block 52, e.g. by updating values of parameters included in the model function. The operation of sub-block 55 will be further exemplified in relation to FIGS. 8-9. The sub-block 55 may be omitted, and the sub-block 52 may be operated with a fixed (pre-defined) model function.

Figure 6:
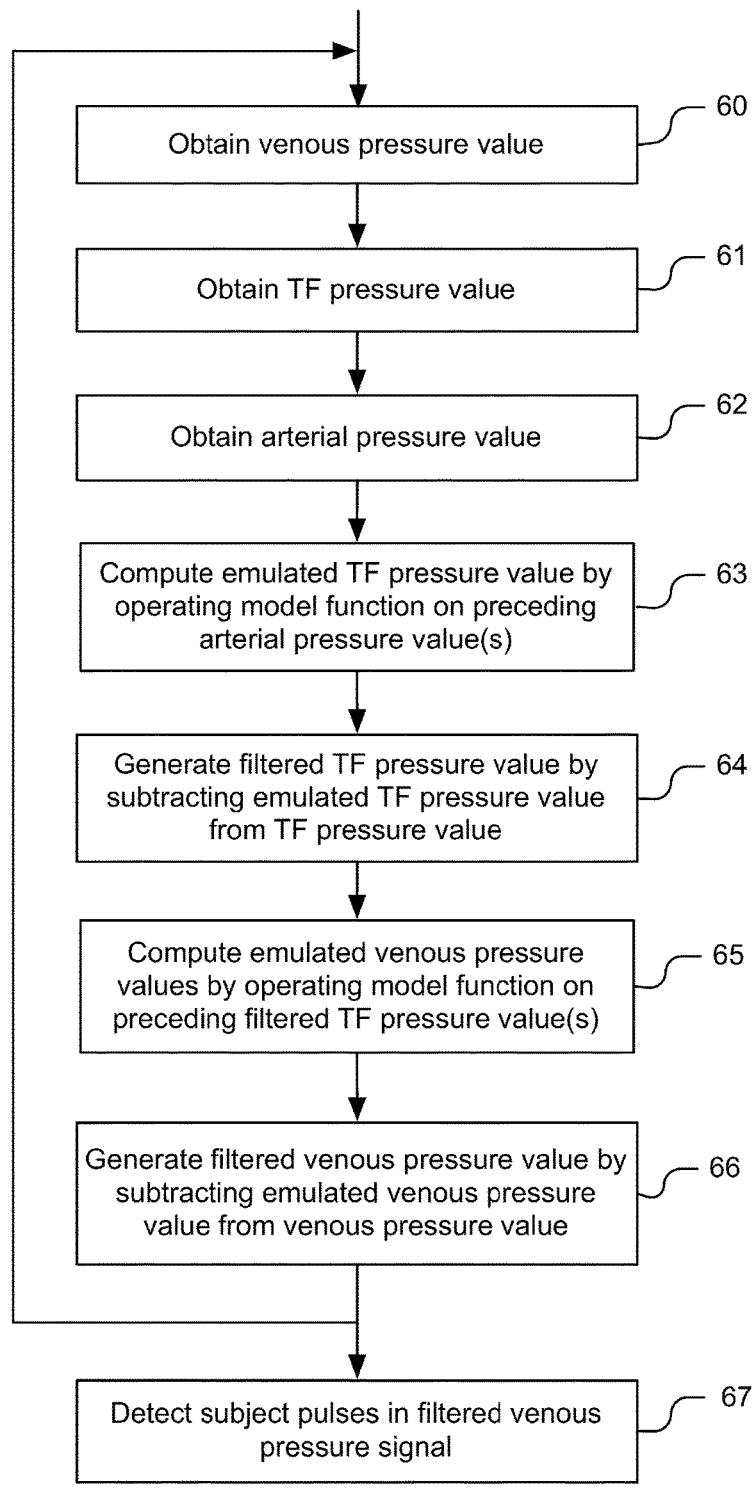
FIG. 6 is a flow chart of a monitoring method according to another embodiment.

FIG. 6 is a flow chart of a method that has been developed to improve the filtered signal $y_f$ if the TF signal u includes subject pulses, i.e. signal components that originate from the physiological source PH in FIG. 1. In the apparatus of FIG. 1, such signal components are generated by pressure waves that propagate from the source PH through the cardiovascular system of the subject to the vascular access 3, and via the access device 2″ through the EC circuit $1a$ to the dialyzer 5 and into the TF circuit $1b$. In the method of FIG. 4, these signal components may cause at least part of the subject pulses to be represented in the emulated venous signal ŷ; and thereby affect the appearance of the subject pulses in the filtered signal $y_f$. For example, the subject pulses may be distorted in shape or decreased in magnitude in the filtered signal $y_f$. This problem is typically aggravated with increasing magnitude of the subject pulses in the TF signal u compared to the venous signal y.

As noted above, the arterial signal v (in absence of pump pulses) contains subject pulses and is essentially free of disturbances from the TF circuit $1b$. The method in FIG. 6 is based on the insight that the technique for generating the emulated venous signal ŷ; may be similarly applied to generate an emulated TR signal û, which mimics the appearance of the subject pulses in the TR signal u. By subtracting the emulated TR signal a from the TR signal u, the influence of the subject pulses may be reduced or even eliminated in the TR signal that is used for generating the emulated venous signal ŷ.

In FIG. 6, the filtering operation involves steps 60-66. Steps 60, 61 are identical to steps 40, 41 in FIG. 4 and result in signal values y(t) and u(t). In step 62, an arterial pressure value $v_{raw}(t)$ is obtained from the arterial sensor $6c$. The following discussion assumes that step 62 also involves the above-mentioned pre-processing, resulting in a signal value v(t) (even if the pre-processing may be omitted). In step 63, an emulated TF signal value û(t) is computed, and in step 64 a filtered TF signal value $u_f(t)$ is generated by subtracting the emulated TF signal value û(t) from the TF signal value u(t). Step 63 may be implemented similarly to step 42, although a different model function may be used. Generally, the emulated TR signal value û(t) is thus computed based on at least one preceding arterial signal value, i.e. a signal value generated by step 62 at a preceding time point, e.g. the immediately preceding time point t−1 Like in step 42, it is conceivable that step 63 determines the signal value û(t)

based on a plurality of arterial signal values and a plurality of TF signal values generated at preceding time points. Step 65 is identical to step 42, but operates on the filtered TF signal $u_f$ instead of the TF signal u, and results in an emulated venous signal value $\hat{y}(t)$. Step 66 is identical to step 43 and results in a filtered venous signal value $y_f(t)$. Step 67 is identical to step 44.

Figure 7:
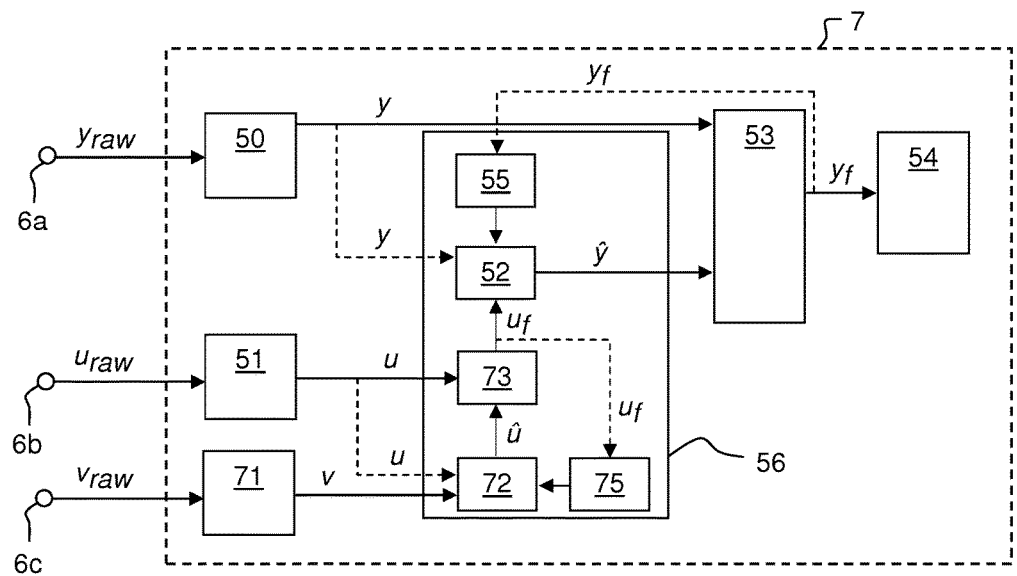
FIG. 7 is a block diagram of a structure for implementing the method in FIG. 6.

FIG. 7 is a block diagram of a structure for implementing the method of FIG. 6 in the device 7. The input blocks 50, 51, the subtraction block 53 and the pulse detection block 54 implement step 60, step 61, step 66 and step 67, respectively, and are identical to the corresponding blocks in FIG. 5. The input block 71 implements step 62 and is arranged to obtain the arterial signal $v_{raw}$ from the arterial sensor 6c and output a sequence of arterial signal values v(t). Like in FIG. 4, the emulation block 56 is configured to compute a sequence of emulated signal values $\hat{y}(t)$. Block 56 includes an emulation sub-block 72 which implements step 63 and is configured to compute a sequence of emulated TF signal values $\hat{u}(t)$, based on the sequence of arterial signal values v(t), and optionally based on the sequence of TF signal values u(t). Block 56 further includes a subtraction sub-block 73 which implements step 64 and is configured to compute a sequence of filtered TF signal values $u_f(t)$, based on the sequence of TF signal values u(t) and the sequence of emulated TF signal values $\hat{u}(t)$. Block 56 further includes the sub-block 52 which implements step 65 and is configured to compute a sequence of emulated venous signal values $\hat{y}(t)$, based on the sequence of filtered TF signal values $u_f(t)$, and optionally based on the sequence of venous signal values y(t). Sub-block 52 in FIG. 7 may be identical to sub-block 52 in FIG. 5. In the illustrated example, block 56 also includes sub-blocks 55 and 75 which are configured to intermittently or continuously update the model functions that are used by sub-block 52 and sub-block 72, respectively. Sub-block 55 in FIG. 7 may be identical to sub-block 55 in FIG. 5, and sub-block 75 may be similar to sub-block 55, although a different model function may be used.

Examples of Model Functions

Below follows a detailed example of how a model function may be designed and used for generating the emulated venous signal $\hat{y}$; based on the TF signal u. The detailed example is concluded with a description of a practical implementation with reference to the flow chart in FIG. 8.

In the following example, the model function is based on a dynamic model. Dynamic models are models that describe the dynamic behavior of a system, i.e. how signals vary with time. One common type of dynamic model is the input/output model, which describes how an input will dynamically affect an output. A common type of input/output models in continuous time is defined by a differential equation of some order linking the input and output. For processing in computers, continuous time input/output models are commonly transferred into models in discrete time, which only relate input and output at discrete points in time. A discrete time input/output model based on an n:th order ordinary linear differential equation is given by $$y(t)+a_1 \cdot y(t-1)+ \ldots +a_n \cdot y(t-n)=b_1 u(t-1)+ \ldots +b_n \cdot u(t-n) \quad (1)$$

in which the sum of the measured output value y(t) at current time t, and a weighted sum of n preceding time points in the output signal y is equal to a weighted sum of n preceding time points within the input signal u. In Eq. 1 there is no direct influence on the current output value y(t) from the current input value u(t). This is a common assumption, and corresponds to a continuous time model where there is no immediate response in the output signal on changes in the input signal (only via the differential equation). Eq. 1, which represents an IIR (Infinite Impulse Response) filter, assumes that there are no disturbances acting on the signals, and that all variations in y are explained by variations in u. In the apparatus of FIG. 1, we know that the output signal y (i.e. the venous pressure signal) is not only influenced by the input signal u (i.e. the TF signal), but also by other signals (subject pulses) as well as measurement noise. This may be accounted for by introducing a noise term e(t):

$$y(t)+a_1 \cdot y(t-1)+ \ldots +a_n \cdot y(t-n)=b_1 \cdot u(t-1)+ \ldots +b_n \cdot u(t-n)+e(t) \quad (2)$$

Eq. 2 is the model used to describe the relation between the measured pressure signals y and u. This type of model is commonly known as an ARX model or a Controlled AutoRegressive model. One aim of the modeling is to find the parameter values ($a_1$ to $a_n$ and $b_1$ to $b_n$) in Eq. 2 that give the best fit to the measured values for u and y. This may be achieved by finding the parameter values that minimize the noise term e(t) in Eq. 2.

The determination of the number of parameters in the model is a matter of model optimization, which lies within the competence of the skilled person. It should be noted that the number of a-parameters may be different from the number of b-parameters, although they are assumed to be equal in this example.

At a given time point s, the best fit in a least squares sense may be found by minimizing a loss function V(s) with respect to the a- and b-parameters:

$$V(s)=\Sigma[y(t)+a_1 \cdot y(t-1)+ \ldots +a_n \cdot y(t-n)-b_1 \cdot u(t-1)- \ldots -b_n \cdot u(t-n)]^2 \quad (3)$$

where the summation ($\Sigma$) is done for all preceding time points, i.e. at least from t=n to t=s. The parameter values that minimize the loss function V(s) may be found analytically, as will be shown in the following. For practical reasons, Eq. 2 may be rewritten in condensed form as:

$$y(t)=\varphi(t)^T \cdot x + e(t) \quad (4)$$

where x is a column vector of parameters, $x=[a_1 \ldots a_n, b_1 \ldots b_n]^T$, and $\varphi(t)$ is a measurement vector of preceding output values and input values, $\varphi(t)=[-y(t-1) \ldots -y(t-n) u(t-1) \ldots u(t-n)]^T$, where superscript T denotes the transpose of a vector. In the present disclosure, all vectors and matrices are given in bold characters.

Using this notation, Eq. 3 may be rewritten as:

$$V(s)=\Sigma[y(t)-\varphi(t)^T \cdot x]^2 \quad (5)$$

The parameter values that minimize this function at time s are the optimal least squares estimates of the parameters x and are denoted $x_e(s)$. It may be analytically shown that these estimated parameter values are given by:

$$x_e(s)=(\Sigma[\varphi(t) \cdot \varphi(t)^T])^{-1} \cdot (\Sigma[y(t) \cdot \varphi(t)]) \quad (6)$$

In a computation-efficient implementation, Eq. 6 is rewritten in a recursive way, so that the current parameter estimate $x_e(s)$ may be obtained by updating the preceding parameter estimate $x_e(s-1)$, rather than re-evaluating Eq. 6 at each time s. This may be achieved by introducing an intermediate matrix P(s) given by:

$$P(s)=(\Sigma[\varphi(t) \cdot \varphi(t)^T])=P(s-1)^{-1} \quad (7)$$

For computation efficiency, the intermediate matrix P(s) should also be updated recursively. It may be shown that:

$$P(s)^{-1}=\Sigma[\varphi(t) \cdot \varphi(t)^T]=P(s-1)^{-1}+\varphi(s) \cdot \varphi(s)^T \quad (8)$$

Inverting both sides of Eq. 8 yields:

$$P(s)=P(s-1)-P(s-1)\cdot\varphi(s)\cdot\varphi(s)^T\cdot P(s-1)/(1+\varphi(s)^T\cdot P(s-1)\cdot\varphi(s)) \quad (9)$$

Introducing Eq. 9 into Eq. 6 yields, after some manipulation:

$$x_e(s)=x_e(s-1)+K(s)\cdot[y(s)-\varphi(s)^T\cdot x_e(s-1)] \quad (10)$$

where the gain vector K(s) is defined as:

$$K(s)=P(s-1)\cdot\varphi(s)/(1+\varphi(s)^T\cdot P(s-1)\cdot\varphi(s)) \quad (11)$$

Together Eq. 9, Eq. 10 and Eq. 11 define a method for recursively updating $x_e(s)$, i.e. the values of the parameters in the model function.

The last term in Eq. 10, $\varphi(s)^T\cdot x_e(s-1)$, is the prediction by the model at time s−1 of the next measurement value y(s). Thus, the emulated venous signal value at time s is given by:

$$\hat{y}(s)=\varphi(s)^T\cdot x_e(s-1) \quad (12)$$

Figure 8:
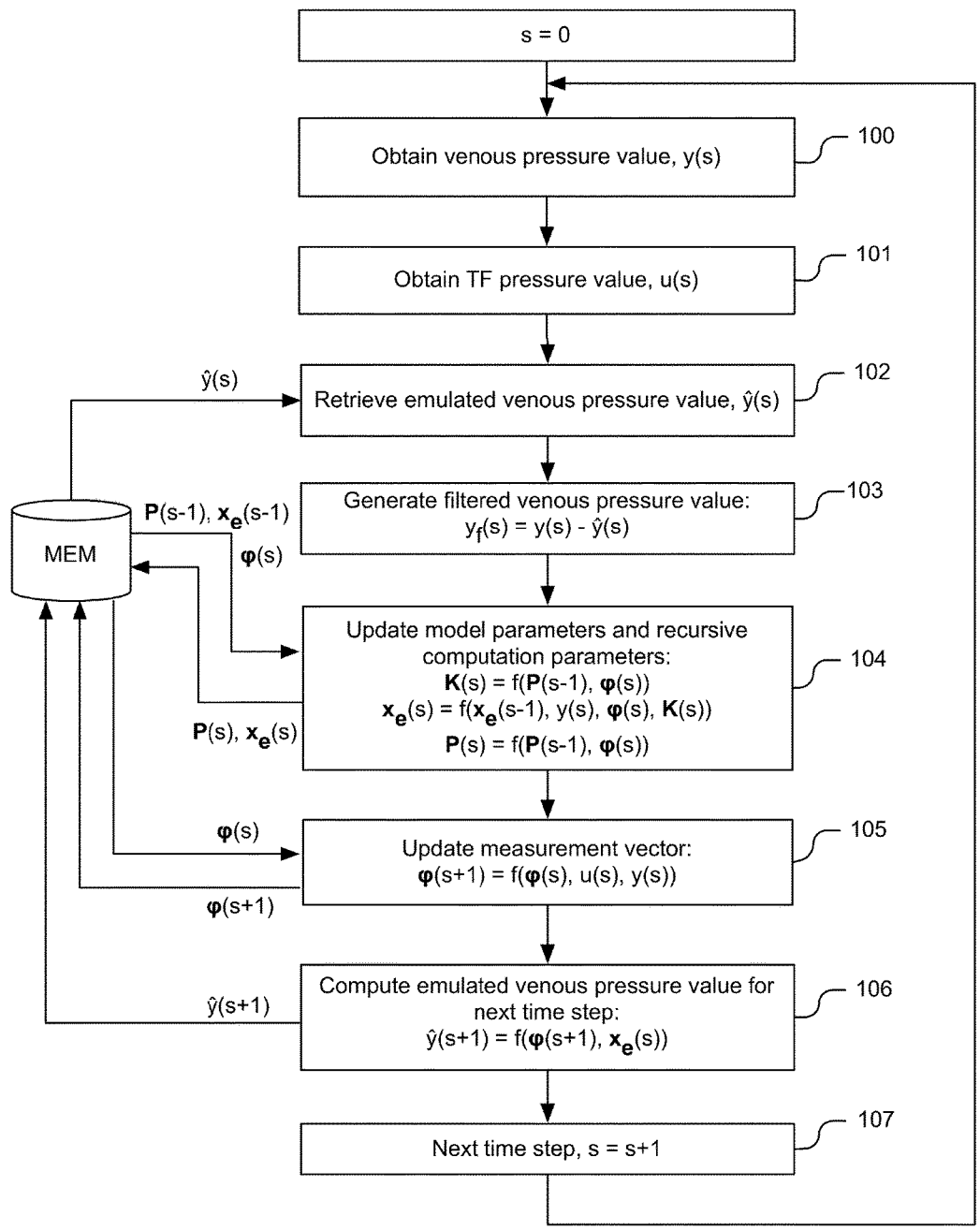
FIG. 8 is a flowchart of an implementation of the monitoring method in FIG. 4.

FIG. 8 is a flowchart of a practical implementation of the filtering operation in FIG. 4 that uses the foregoing model function for computing the emulated venous pressure and recursively updates the model function. Thus, steps 100-107 in FIG. 8 correspond to steps 40-43 in FIG. 4 and may be implemented by blocks 50, 51, 53 and 56 in FIG. 5. Specifically, step 100 corresponds to step 40 (implemented by block 50), and step 101 corresponds to step 41 (implemented by block 51), steps 102, 105 and 106 correspond to step 42 (implemented by block 56, in particular sub-block 52), step 103 corresponds to step 43 (implemented by block 53), and step 104 is a step of updating the model function (implemented by block 56, in particular sub-block 55). In FIG. 8, time is represented by the variable s, which is incremented in step 107 for each sequence of steps 100-106.

In FIG. 8, the emulated venous signal value is generated by prediction in step 106 at one time step and used for filtering in step 103 at the next time step. Looking at the emulation operations at time s in more detail, step 102 retrieves the emulated venous signal value $\hat{y}(s)$, which was stored in MEM by step 106 at time s−1. Step 103 generates the filtered signal value $y_f(s)$ by subtracting the emulated venous signal value $\hat{y}(s)$ from the venous signal value y(s) obtained by step 100. Step 105 updates the measurement vector to include the current values y(s) and u(s) obtained by steps 100 and 101. It should be noted that, according to the model (Eq. 2), the measurement vector $\varphi(s)$ should contain most recent preceding output values y within a time window of length n and the most recent input values u within a time window of length n. In the general case, as explained above, these time windows may have different length. In one extreme, the number of preceding output values y may be zero (resulting in a FIR filter, see below).

Figure 9:
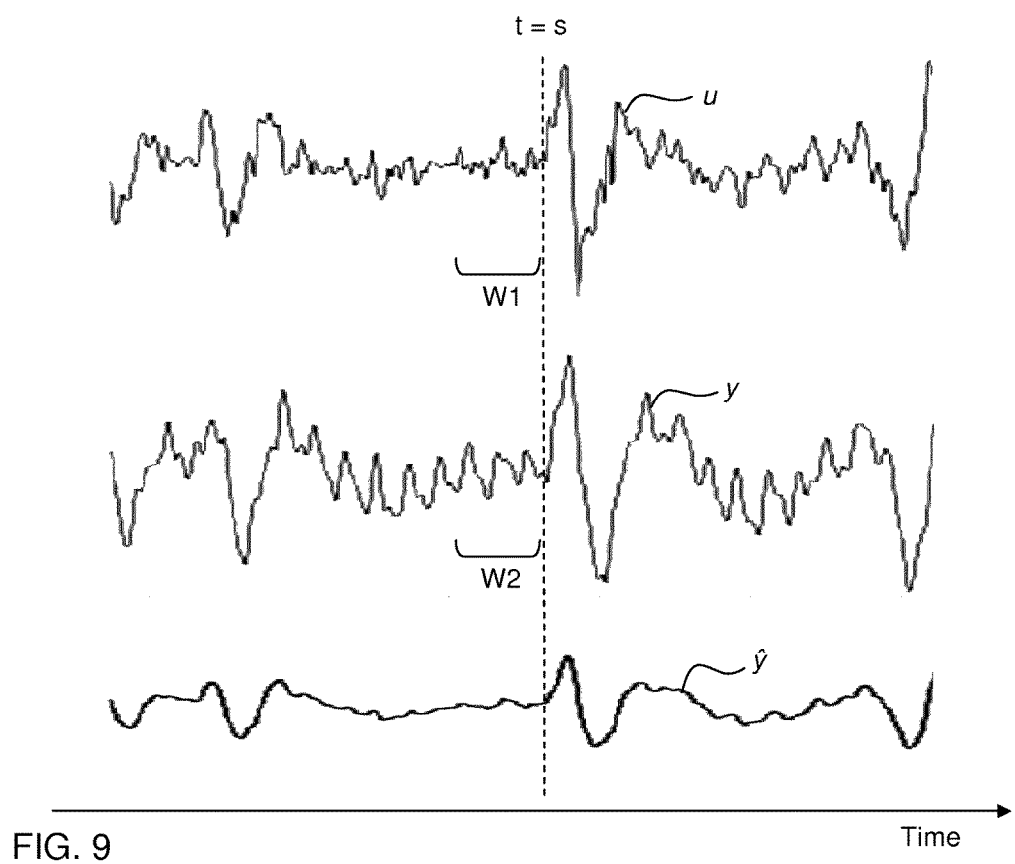
FIG. 9 illustrates the use of time windows when generating emulated signal values in accordance with an embodiment.

The use of time windows is further exemplified in FIG. 9, which shows an example of a TF signal u, a venous signal y and an emulated venous signal $\hat{y}$. At time t=s, the values within time windows W1, W2 are included in the measurement vector $\varphi(s)$ and are used for computing the emulated value $\hat{y}(s)$. At the next time step, for computing $\hat{y}(s+1)$, the time windows W1, W2 are also shifted one step in time. The moving time windows W1, W2 are implemented by updating of the measurement vector $\varphi(s)$ in step 105, e.g. $\varphi(s+1)$ may be obtained by retrieving the current measurement vector $\varphi(s)$, and by shifting the elements of $\varphi(s)$ and inserting y(s) and u(s). The updated measurement vector $\varphi(s+1)$ is stored in MEM, for retrieval by steps 104 and 105 at the next time step. In step 106, the emulated venous signal value $\hat{y}(s+1)$ for the next time step is calculated according to Eq. 12 and stored in MEM.

Based on FIG. 9, it is understood that the emulated signal value $\hat{y}(s)$, according to Eq. 12, is given by a weighted sum of the preceding signal values within time window W2 and the preceding signal values within time window W1, where the a-parameters and the b-parameters are weighting factors in the weighted sum.

The model updating step 104 operates to retrieve the intermediate matrix P(s−1), the parameter estimate $x_e(s-1)$ and the current measurement vector $\varphi(s)$ that were computed and stored in MEM by steps 104 and 105 at time s−1. Then, step 104 computes the gain vector K(s) according to Eq. 11, and the parameter estimate $x_e(s)$ according to Eq. 10. Step 104 also updates the intermediate matrix P(s−1) according to Eq. 9. The resulting data items $x_e(s)$, P(s) are stored in MEM, for retrieval by step 104 at the next time step. Here, it may be noted that Eq. 10 actually corresponds to $x_e(s)=x_e(s-1)+K(s)\cdot y_f(s)$. This means that the computation of $x_e(s)$ may be made more efficient by implementing step 104 to re-use the filtered signal value $y_f(s)$ that was just generated in step 103. In the block diagrams of FIG. 5 and FIG. 7, this corresponds to sub-block 55 obtaining the filtered signal $y_f$ from the filtering block 53, as indicated by a dashed arrow.

If it may be assumed that the disturbance e(t) in Eq. 2 is white noise, i.e. that the values of e at different times are uncorrelated, the parameter estimates in the vector $x_e$ will converge over time. The intermediate matrix P will then be the covariance matrix of the vector $x_e$ scaled with the variance of e, and P will decrease to zero with time. The process in FIG. 8 may be started by setting $x_e(0)=0$, and P(0) may be a diagonal matrix with large diagonal elements.

If the values of e at different times are not uncorrelated, Eq. 2 may be modified into:

$$y(t)+a_1\cdot y(t-1)+\ldots+a_n\cdot y(t-n)=b_1\cdot u(t-1)+\ldots+b_n\cdot u(t-n)+e(t)+c_1\cdot e(t-1)+\ldots+c_n\cdot e(t-n) \quad (13)$$

This type of model is commonly known as an ARMAX model or Controlled AutoRegressive Moving Average model (Controlled ARMA model). Eq. 12 is equally applicable to this type of model, albeit with $x_e$ containing the estimates of the a-, b- and c-parameters and the measurement vector being defined as $\varphi(s)=[-y(s-1)\ldots-y(s-n)u(s-1)\ldots u(s-n)e(s-1)\ldots e(s-n)]^T$, where the noise terms $e(s-1)\ldots e(s-n)$ are estimated by the model. Estimating the a-, b- and c-parameters is typically a more complicated task than for the above-described ARX model. For example, the parameters may be estimated using the maximum likelihood method or the instrumental variable method, which are well known to the person skilled in the art.

In a variation, the process in FIG. 8 may be configured to disable the parameter updating step 104 when the parameter estimates in the vector $x_e$ have converged. Thus, the model function is updated (parameterized) during a start-up phase, and then the process switches to use the converged values of the parameter estimates $x_e$ in step 106.

In a further variation, step 104 may be omitted, step 106 may use pre-defined values of the parameter estimates $x_e$ for generating the emulated signal values $\hat{y}$.

In certain situations, it is conceivable that the values of the model function parameters change during operation of the process in FIG. 8 and it may be desirable to modify step 104 such that the parameter estimates $x_e$ follow time-variations in the a- and b-parameters rather than converge. Such time-variations in the model parameters may e.g. result from changes in the rotational speed of the blood pump 4, movement of the tubings in the EC circuit 1a, accumulation of deposits in the EC circuit 1a, the dialyzer 5 or the TF circuit 1b, etc. Below follows examples of how step 104 may be modified to represent these time-variations.

In one example, the summation (Σ) in the loss function in Eq. 3 is done only a limited number of steps backwards in time (i.e. not from the start). This approach does not allow for the use of recursive equations, but requires the parameter estimates to be calculated using Eq. 6. The model parameters will then describe the behavior of the system during the time window used in the summation and will change as the window moves.

In another example, which may be more computation efficient, the loss function in Eq. 3 is modified to include a weighting function that decreases the influence of old terms, e.g. exponentially. In one implementation, the loss function V(s) is given by $$V(s)=\Sigma \lambda^{s-t} \cdot [y(t)+a_1 \cdot y(t-1)+ \ldots +a_n \cdot y(t-n) - b_1 \cdot u(t-1) - \ldots - b_n \cdot u(t-n)]^2 \quad (14)$$

where a global weighting factor $\lambda<1$ is introduced, so that $\lambda^{s-t}$ decreases with decreasing t. This results in a minor modification of the equations for calculating P(s), $x_e$(s) and K(s):

$$P(s)=[P(s-1)-P(s-1)\cdot\varphi(s)\cdot\varphi(s)^T\cdot P(s-1)/(\lambda+\varphi(s)^T\cdot P(s-1)\cdot\varphi(s))]/\lambda \quad (15)$$

$$x_e(s)=x_e(s-1)+K(s)\cdot[y(s)-\varphi(s)^T x_e(s-1)] \quad (16)$$

$$K(s)=P(s-1)\cdot\varphi(s)/(\lambda+\varphi(s)^T P(s-1)\varphi(s)) \quad (17)$$

The effect of λ is to prevent the intermediate matrix P from converging to zero, which means that the gain vector K will not go to zero, and the parameter estimates $x_e$ will never converge. In certain situations, e.g. if the signals y and u do not vary enough, the matrix P may have some eigenvalues that will increase towards infinity, which may lead to numerical instability.

In another example, which may overcome the risk for numerical instability, Eq. 9, 10 and 11 may be modified by simply adding a constant matrix R to Eq. 9:

$$P(s)=P(s-1)-P(s-1)\cdot\varphi(s)\cdot\varphi(s)^T\cdot P(s-1)/(1+\varphi(s)^T\cdot P(s-1)\cdot\varphi(s))+R \quad (18)$$

The matrix R is a constant positive semidefinite matrix of the same order as the matrix P(s), and at least a subset of the values in R are non-zero. This corresponds to an assumption that the model parameters are not constant, but that they change between each point in time with a random vector having covariance matrix R. Thus, Eq. 18 will also prevent P from converging to zero.

Generally, all of the different model functions with recursive updating of the model parameter values, as described in the foregoing, may be summarized by the following set of equations:

$$x_e(s)=x_e(s-1)+[P(s-1)\cdot\varphi(s)/(\lambda+\varphi(s)^T P(s-1)\cdot\varphi(s))]\cdot[y(s)-\varphi(s)^T x_e(s-1)] \quad (19)$$

$$P(s)=[P(s-1)-P(s-1)\cdot\varphi(s)\cdot\varphi(s)^T\cdot P(s-1)/(1+\varphi(s)^T\cdot P(s-1)\cdot\varphi(s))]/\lambda+R \quad (20),$$

where the global weighting factor $\lambda \le 1$ and R is a constant positive semidefinite matrix.

If the model parameters are fixed (time-invariant), Eq. 19 and 20 may be implemented with λ=1 and R being a constant positive semidefinite matrix with all values set to zero (a "zero matrix").

If the model parameters are time-varying, in a first variant, Eq. 19 and 20 may be implemented with λ<1 and R being a constant positive semidefinite matrix with all values set to zero. In a second variant, Eq. 19 and 20 may be implemented with λ=1 and R being a constant positive semidefinite matrix, in which at least a subset of the constant values are non-zero. A combination of the first and second variants is also conceivable, in which Eq. 19 and 20 are implemented with λ<1 and R being a constant positive semidefinite matrix, in which at least a subset of the constant values are non-zero.

There are also ARX models that have been developed for time-varying systems in other fields of technology that may be used, e.g. as described in the article "ARX models for time-varying systems estimated by recursive penalized weighted least squares method" by Qin et al, published in *Journal of Math-for-Industry*, vol. 2 (2010A-11), pp. 109-114, and in references therein.

It should be noted that it is possible to define Eq. 1 to represent an FIR (Finite Impulse Response) filter, instead of an IIR filter. This corresponds to setting all a-parameters to zero, and all of the above equations are equally applicable to a dynamic model given by Eq. 2 with only b-parameters. When such a model function is used, the emulated venous signal values are only computed as a function of preceding signal values in the TF signal u. Specifically, each emulated venous signal value ŷ(s) is computed as a weighted sum of the preceding signal values in the TF signal u within the time window W1 (cf. FIG. 9). Thus, the use of the venous signal y in sub-block 52 is optional (depending on the model function), hence the dashed arrow from block 50 to sub-block 52 in FIG. 5 and FIG. 7.

It also should be understood that the foregoing model functions, and the different variations and examples, are equally applicable for generating the emulated TF signal û based on the arterial signal v, by substituting ŷ for û and u for v in the equations above. In such an embodiment, any updating of model parameters for use in the computation of the emulated TF signal û (according to step 104) may be implemented by sub-block 75 in FIG. 7. As understood from the foregoing, the use of the TF signal u in sub-block 72 is optional (depending on the model function), hence the dashed arrow from block 51 to sub-block 72 in FIG. 7. Also, in analogy with the re-use of the filtered venous signal $y_f$ by sub-block 55 when computing the parameter estimate $x_e$(s) (cf. dashed arrow from block 53 to sub-block 55), sub-block 75 may re-use the filtered TF signal $u_f$ when computing the corresponding parameter estimate for the model function used by sub-block 72, as indicated by the dashed arrow from sub-block 73 to sub-block 75 in FIG. 7.

As an alternative to the input/output models described in the foregoing, the model function may be implemented as an artificial neural network. Such a network also contains coefficients or parameters that are determined from old data (training of the network), and may be used to predict future measurement values. By adequate configuration and training, such a neural network may, e.g., provide an emulated venous signal value 5; based one or more preceding signal values in the TF signal u, optionally in combination with one or more preceding signal values in the venous signal y.

Example of Dialysis Machine

FIG. 10 serves to give a more detailed example of a blood processing apparatus 1, implemented as a dialysis machine, and the practical use of the inventive monitoring. The dialysis machine 1 comprises an EC circuit 1a which includes a connection system C for establishing fluid communication between the EC circuit 1a and the vascular system of a patient. The connection system C comprises an arterial access device 2' (here in the form of an arterial needle), a connection tube segment 10a and a connector C1a. The connection system C also comprises a venous access device 2" (here in the form of a venous needle), a connection tube segment 11a and a connector C2a. The connectors C1a, C2a are arranged to provide a releasable or permanent engagement with a corresponding connector C1b, C2b. The connectors C1a, C1b, C2a, C2b may be of any known type. In certain implementations, the connectors C1a, C1b, C2a, C2b may be omitted, whereby the connection system C consists of the access devices 2', 2".

In FIG. 10, the EC circuit 1a further comprises an arterial tube segment 10b, and a blood pump 4 which may be of peristaltic type. On the arterial side of the blood pump 4 there is an arterial pressure sensor 6c which measures the pressure upstream of the pump 4 in the arterial tube segment 10b. The pump 4 forces the blood, via a tube segment 12, to the blood-side of the dialyzer 5. The illustrated dialysis machine 1 is additionally provided with a pressure sensor 6d ("system pressure sensor") that measures the pressure between the blood pump 4 and the dialyzer 5. The blood is led via a tube segment 13 from the blood-side of the dialyzer 5 to a venous drip chamber or deaeration chamber 14 and from there back to the connection system C via a venous tube segment 11b and the connector C2b. A venous pressure sensor 6a is provided to measure the pressure on the venous side of the dialyzer 5, here in the venous drip chamber 14.

In the example of FIG. 10, the venous side of the EC circuit 1a is made up of tube segment 12, the blood-side of the dialyzer 5, tube segment 13, drip chamber 14, tube segment 11b, connectors C2a, C2b, tube segment 11a, and the venous access device 2", and the arterial side is made up of tube segment 10b, connectors C1a, C1b, tube segment 10a, and the arterial access device 2'.

Both the arterial needle 2' and the venous needle 2" are configured to be connected to a vascular access (cf. 3 in FIG. 1). Depending on the type of vascular access, other types of access devices may be used instead of needles, e.g. catheters. The vascular access 3 may be of any suitable type, including different types of venovenous (VV) blood accesses and different types of arteriovenous (AV) access, such as a graft or a fistula.

The dialysis machine 1 also comprises a TF circuit 1b, here exemplified as a source 16a of treatment fluid ("dialysis fluid"), a tube segment 17, a TF-side of the dialyzer 5, a tube segment 18a, a TF fluid pump 19, a tube segment 18b, and an outlet/drain 16b. It is to be understood that FIG. 10 is schematic and exemplary, and that the TF circuit 1b may include other components, such as further pumps, further flow paths, flow-controlling valves, chambers, etc. A TF pressure sensor 6b is provided to measure the fluid pressure in the TF circuit 1b. The source 16a may comprise a fluid generation unit that produces the treatment fluid from one or more concentrates and water, and optionally performs degassing and heating of the treatment fluid and controls its flow rate and pressure.

The dialysis machine 1 further comprises a central control unit 122 that controls the operation of the dialysis machine 1. In FIG. 10, the control unit 122 is connected to operate the pumps 4, 19, various valves (not shown), clamping devices (represented by 123), and to acquire data from the pressure sensors 6a-6d. Although not shown or discussed further it is to be understood that the control unit 122 may implement many different functions, e.g. various safety functions, controlling the temperature and composition of the treatment fluid, controlling additional pumps, etc.

In the illustrated example, the monitoring device 7 is connected by data lines to the pressure sensors 6a, 6b and 6c, so as to acquire the pressure signals $y_{raw}$, $u_{raw}$ and $v_{raw}$, which are designated by P6a, P6b and P6c, respectively, in FIG. 10. The device 7 is also connected by a data line to the control unit 122 for transmitting a control signal CTRL that may, e.g., cause the control unit 122 to change the revolution speed of the blood pump 4, or cause the control unit 122 to stop the blood pump 4 and activate one or more clamping devices 123 (only one shown) on the tube segments 10b, 11b, 12, 13. The device 7 may also be tethered or wirelessly connected to further devices, indicated by 128, e.g. an alarm unit for generating an audible/visual/tactile alarm or other warning signal, a display for displaying information related to the monitoring, etc. The device 7 may be implemented as a separate unit connected to the dialysis machine 1 (as shown), or it may be incorporated as part of the dialysis machine 1, e.g. as part of the control device 122.

In all embodiments disclosed herein, the device 7 may be configured to monitor the operation of the EC circuit 1a and/or the physiological state of the subject, by detecting and analyzing the subject pulses in the filtered venous signal $y_f$. This functionality may be implemented in the pulse detection block 54 (FIG. 5 and FIG. 7) or in a dedicated block in the device 7 that operates on an output of the pulse detection block 54.

In one example, the device 7 is configured to identify a disruption of the connection system C on the venous-side of the EC circuit 1a by analyzing the subject pulses in the filtered venous signal $y_f$. Such a disruption is indicated by absence of the subject pulses. The disruption may be caused by a dislodgement of the access device 2" from the blood vessel access, i.e. that the access device 2" comes loose from the vascular system of the subject. Alternatively, the disruption may be caused by a disconnection of the access device 2" from the EC circuit 1a, typically by disruption/defective coupling/uncoupling of the connectors C2a, C2b. Any known technique may be implemented in the device 7 for detecting the absence of subject pulses and identifying the disruption, e.g. as disclosed in WO97/10013, WO2009/156174, WO2010/149726, US2005/0010118, and US2010/0234786. It is to be noted that detecting absence of subject pulses in the filtered venous signal $y_f$ may involve comparing the filtered venous signal $y_f$ to the arterial signal v, e.g. by cross-correlation as described in WO2009/156174.

In another example, the device 7 is configured to identify a reversed connection of the EC circuit 1a to the vascular access 3, e.g. caused by reversed positioning of the access devices 2', 2" in the vascular access 3 or reversed connection of connectors C1b, C2b to connectors C1a, C2a, by analyzing at least one of the shape and the timing of subject pulses in the filtered venous signal $y_f$ and in the arterial signal v, e.g. as disclosed in WO2011/080188.

In yet another example, the device 7 is configured to monitor a functional state or functional parameter of the cardiovascular system of the subject by analyzing the subject pulses, e.g. when the subject pulses originate from the heart, the breathing system or the blood pressure regulating system of the subject. Such uses of the filtered signal include detecting, presenting, tracking and predicting vital signs, e.g. cardiac or respiratory related such as heart pulse rate, blood pressure, cardiac output, blood flow rate through the blood vessel access ("access flow"), arterial stiffness, as well as identifying signs of stenosis formation within the blood vessel access, predicting rapid symptomatic blood pressure decrease and detecting, tracking and predicting various breathing disorders. All of these uses or applications may be based on extraction and analysis of at least one of the shape, the magnitude and the timing of the subject pulses in the filtered venous signal $y_f$, e.g. as disclosed in WO2010/149726, WO2011/080186, WO2011/080189, WO2011/080190, WO2011/080191 and WO2011/080194.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the pressure sensor may be of any type, e.g. operating by resistive, capacitive, inductive, magnetic, acoustic or optical sensing, and using one or more diaphragms, bellows, Bourdon tubes, piezo-electrical components, semiconductor components, strain gauges, resonant wires, accelerometers, etc. For example, the pressure sensor may be implemented as a conventional pressure sensor, a bioimpedance sensor, a photoplethysmography (PPG) sensor, etc.

Likewise, the blood pump may be of any type, not only a rotary peristaltic pump as indicated above, but also any other type of positive displacement pump, such as a linear peristaltic pump, a diaphragm pump, or a centrifugal pump.

Furthermore, the inventive monitoring technique is not limited to filtering of venous pressure signals, but may be used for filtering any pressure signal from a pressure sensor in an extracorporeal blood circuit in a blood processing apparatus as long as the pressure signal includes both subject pulses and signal interferences that enters the extracorporeal blood circuit from a treatment fluid supply system, via a blood processing unit.

Further, the inventive technique is applicable for monitoring in all types of extracorporeal blood flow circuits in which blood is taken from the systemic blood circuit of the patient to interact with a treatment fluid in a blood processing unit and is then returned to the patient. Such blood flow circuits include circuits for hemodialysis, hemofiltration, hemodiafiltration, continuous renal replacement therapy, and extracorporeal liver support/dialysis. The extracorporeal blood flow circuit may be connected to the patient by separate access devices for blood removal and blood return, or by a common access device ("single-needle").

The invention claimed is:

1. An apparatus for extracorporeal blood processing comprising:
    an extracorporeal blood circuit for connection to the vascular system of a subject;
    a blood processing unit in the extracorporeal blood circuit;
    a blood pumping device in the extracorporeal blood circuit operable to pump blood through the blood processing unit;
    a treatment fluid supply system operable to pump treatment fluid through the blood processing unit;
    a first pressure sensor arranged in the extracorporeal blood circuit to detect pressure variations in the blood which is pumped through the blood processing unit;
    a second pressure sensor arranged in the treatment fluid supply system to detect pressure variations in the treatment fluid which is pumped through the blood processing unit; and
    a monitoring device including
        a first input block configured to obtain a first pressure signal (y) from the first pressure sensor, wherein the extracorporeal blood circuit is connected to a vascular system of a subject,
        a second input block configured to obtain a second pressure signal (u) from the second pressure sensor,
        an emulation block configured to generate, as a function of the second pressure signal (u), an emulated first pressure signal ($\hat{y}$) which emulates a signal response of the first pressure sensor concurrently over a period of time of the first pressure signal of the first pressure sensor,
        a filtering block configured to generate a filtered signal ($y_f$) as a function of the first pressure signal (y) and the emulated first pressure signal ($\hat{y}$), so as to suppress, in the filtered signal ($y_f$) compared to the first pressure signal (y), signal interferences originating from the treatment fluid supply system, and
        a pulse detection block configured to process the filtered signal ($y_f$) for detection of subject pulses originating from the subject.

2. The apparatus of claim 1, wherein the emulated first pressure signal ($\hat{y}$) is generated as a time sequence of emulated signal values, and wherein the emulation block is configured to generate each emulated signal value to represent an instant signal response of the first pressure sensor as a function of one or more preceding signal values in the second pressure signal (u).

3. The apparatus of claim 2, wherein the emulation block is configured to generate each emulated signal value to represent an instant signal response of the first pressure sensor as a function of preceding signal values in the second pressure signal (u) and as a function of preceding signal values in the first pressure signal (y).

4. The apparatus of claim 2, wherein the emulation block is configured to subtract each emulated signal value from a corresponding signal value of the first pressure signal (y) to generate a filtered signal value in the filtered signal ($y_f$).

5. The apparatus of claim 1, wherein the emulation block is configured to, in the emulated first pressure signal ($\hat{y}$), emulate the signal response of the first pressure sensor with respect to magnitude, shape and timing of the signal interferences originating from the treatment fluid supply system.

6. The apparatus of claim 1, wherein the emulation block is configured to generate the emulated first pressure signal ($\hat{y}$) using a first model function which includes a set of model parameters, wherein the set of model parameters define a weighted sum of preceding signal values within a moving time window of fixed length in the second pressure signal (u) and, optionally, preceding signal values within a further moving time window of fixed length in the first pressure signal (y).

7. The apparatus of claim 6, wherein the first model function is a controlled autoregressive model or a controlled autoregressive moving average model.

8. The apparatus of claim 6, wherein the emulation block is configured to update the set of model parameters as a function of time.

9. The apparatus of claim 8, wherein the emulation block is configured to recursively update the set of model parameters.

10. The apparatus of claim 6, wherein the control unit is configured to repeatedly perform a processing sequence that includes:
   obtaining a signal value of the first pressure signal (y);
   obtaining a signal value of the second pressure signal (u);
   retrieving, by the emulation block, an emulated signal value of the emulated first pressure signal (ŷ), the emulated signal value being calculated in a preceding processing sequence;
   generating, by the filtering block, a filtered signal value by subtracting the emulated signal value from the signal value of first pressure signal (y);
   updating, by the emulation block, a measurement vector to include the signal value of the second pressure signal (u), such that the measurement vector contains the preceding signal values within the moving time window for a subsequent processing sequence;
   optionally updating, by the emulation block, the measurement vector to include the signal value of the first pressure signal (y), such that the measurement vector contains the preceding signal values within the further moving time window for the subsequent processing sequence; and
   calculating, by the emulation block, as a function of the set of model parameters and the updated measurement vector, an emulated signal value for use in a forthcoming processing sequence.

11. The apparatus of claim 10, wherein the emulation block is configured to recursively compute, in each processing sequence, at least during a start-up phase of the monitoring device, a vector $x_e(s)$ containing values of the set of model parameters according to:

$$\begin{cases} x_e(s) = x_e(s-1) + [P(s-1)\cdot\varphi(s)/(\lambda + \varphi(s)^T\cdot P(s-1)\cdot\varphi(s))]\cdot[y(s) - \varphi(s)^T\cdot x_e(s-1)] \\ P(s) = [P(s-1) - P(s-1)\cdot\varphi(s)\cdot\varphi(s)^T\cdot P(s-1)/(1+\varphi(s)^T\cdot P(s-1)\cdot\varphi(s))]/\lambda + R \end{cases}$$

wherein $x_e(s-1)$ is the vector containing values of the set of model parameters as computed in the preceding processing sequence, y(s) is the signal value of the first pressure signal obtained in the current processing sequence, and $\varphi(s)$ is the measurement vector before said updating, P(s) is a matrix, λ is a global weighting factor that is smaller than or equal to 1, and R is a constant positive semidefinite matrix.

12. The apparatus of claim 11, wherein the emulation block is configured to evaluate $[y(s)-\varphi(s)^T\cdot x_e(s-1)]$ by obtaining the filtered signal value generated by the filtering block in the current processing sequence.

13. The apparatus of claim 11, wherein the global weighting factor is smaller than 1,λ1.

14. The apparatus of claim 11, wherein at least a subset of the constant values in R are non-zero.

15. The apparatus of claim 1, wherein the emulation block is configured to generate the emulated first pressure signal by use of a FIR (Finite Impulse Response) filter or an IIR (Infinite Impulse Response) filter.

16. The apparatus of claim 1, wherein the control unit is configured to perform a preparatory filtering to essentially eliminate pressure pulsations that originate from the blood pumping device in the first pressure signal (y) and the second pressure signal (u), respectively.

17. The apparatus of claim 1, wherein the control unit is configured to perform a preparatory filtering to essentially eliminate, in the first pressure signal (y) and the second pressure signal (u), respectively, periodic pressure pulsations that originate in the apparatus for extracorporeal blood processing.

18. The apparatus of claim 1, wherein the second pressure sensor is arranged to sense the subject pulses, wherein the monitoring device further includes a third pressure sensor configured to generate a third pressure signal (v), the third pressure sensor arranged in the extracorporeal blood circuit so as to sense the subject pulses and be essentially isolated from pressure variations originating from the treatment fluid supply system, and wherein the emulation block includes a first sub-block configured to generate, as a function of the third pressure signal (v), an emulated second pressure signal (û) which emulates a signal response of the second pressure sensor concurrently over a period of time of the second pressure signal of the second pressure sensor, a second sub-block configured to generate a filtered second pressure signal ($u_f$) by subtracting the emulated second pressure signal (û) from the second pressure signal (u), and a third sub-block configured to generate the emulated first pressure signal (ŷ) as a function of the filtered second pressure signal ($u_f$).

19. The apparatus of claim 18, wherein the first sub-block is configured to, in the emulated second pressure signal (û), emulate the signal response of the second pressure sensor with respect to the subject pulses.

20. The apparatus of claim 1, wherein the extracorporeal blood circuit extends from a blood withdrawal device, which is connected to the vascular system of the subject, to a blood return device, which is connected to the vascular system of the subject, wherein the first pressure sensor is arranged downstream of the blood pumping device and the blood processing unit in the extracorporeal blood circuit, said monitoring device being configured to signal a dislodgement of the blood return device based on a detected absence of subject pulses in the filtered signal by the pulse detection block.

21. The apparatus of claim 18, wherein the extracorporeal blood circuit extends from a blood withdrawal device, which is connected to the vascular system of the subject, to a blood return device, which is connected to the vascular system of the subject, wherein the first pressure sensor is arranged downstream of the blood pumping device and the blood processing unit in the extracorporeal blood circuit, and the third pressure sensor is arranged upstream of the blood pumping device and the blood processing unit in the extracorporeal blood circuit, said monitoring device being configured to signal a dislodgement of the blood return device based on a detected absence of subject pulses in the filtered signal ($y_f$) by the pulse detection block.

* * * * *